US010365202B2

(12) United States Patent
Ramakrishnan et al.

(10) Patent No.: US 10,365,202 B2
(45) Date of Patent: Jul. 30, 2019

(54) METHOD FOR MEASUREMENT OF ULTRA-LOW PERMEABILITY AND POROSITY BY ACCOUNTING FOR ADSORPTION

(71) Applicant: Schlumberger Technology Corporation, Sugar Land, TX (US)

(72) Inventors: Terizhandur S. Ramakrishnan, Boxborough, MA (US); Michael Supp, Garland, ME (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 22 days.

(21) Appl. No.: 15/151,779

(22) Filed: May 11, 2016

(65) Prior Publication Data
US 2016/0334322 A1 Nov. 17, 2016

Related U.S. Application Data

(60) Provisional application No. 62/159,750, filed on May 11, 2015.

(51) Int. Cl.
*G01N 15/08* (2006.01)
(52) U.S. Cl.
CPC ....... *G01N 15/0826* (2013.01); *G01N 15/088* (2013.01)
(58) Field of Classification Search
CPC ........................ E21B 15/0826; E21B 15/088
See application file for complete search history.

(56) References Cited

U.S. PATENT DOCUMENTS

| 4,543,821 | A | * | 10/1985 | Davis, Jr. | G01N 15/0826 324/376 |
| 4,555,934 | A | | 12/1985 | Freeman et al. | |
| 5,237,854 | A | | 8/1993 | Jones | |
| 5,261,267 | A | * | 11/1993 | Kamath | G01N 15/0826 73/38 |
| 5,544,520 | A | * | 8/1996 | Graf | G01N 15/0826 73/38 |
| 5,832,409 | A | * | 11/1998 | Ramakrishnan | G01N 15/0826 702/12 |
| 6,460,420 | B1 | | 10/2002 | Paul et al. | |
| 6,655,192 | B2 | | 12/2003 | Chavdar | |
| 7,082,812 | B2 | * | 8/2006 | Lenormand | G01N 15/0826 73/38 |
| 7,092,822 | B2 | | 8/2006 | Lenormand et al. | |

(Continued)

FOREIGN PATENT DOCUMENTS

KR     101223462     1/2013

OTHER PUBLICATIONS

"Shale gas provides largest share of U. S. natural gas production in 2013", U.S. Energy Information Administration, [http://www.eia.gov/todayinenergy/detail.cfm?id=18951], Accessed Aug. 16, 2018, 3 pages.

(Continued)

*Primary Examiner* — John Fitzgerald

(57) ABSTRACT

Methods are provided for measuring the permeability and/or porosity of a rock sample having an "ultra-low" permeability while accounting for adsorption. The rock sample may be a sample obtained from a geological formation. The methods account for adsoption of gas within the rock samples.

16 Claims, 8 Drawing Sheets

(56) References Cited

U.S. PATENT DOCUMENTS

| | | | | |
|---|---|---|---|---|
| 7,131,317 | B2* | 11/2006 | Lenormand | G01N 15/0826 73/38 |
| 7,430,895 | B2 | 10/2008 | Liverman et al. | |
| 7,805,982 | B2* | 10/2010 | Hilab | E21B 25/005 73/38 |
| 8,950,252 | B2* | 2/2015 | Haggerty | E21B 49/00 73/152.07 |
| 9,291,541 | B2* | 3/2016 | Kim | G01N 15/0806 |
| 9,709,477 | B2* | 7/2017 | Chertov | G01N 15/082 |
| 9,709,478 | B2* | 7/2017 | Chertov | G01N 15/082 |
| 9,746,410 | B2* | 8/2017 | Chertov | G01N 15/082 |
| 9,989,512 | B2* | 6/2018 | Haggerty | E21B 49/00 |
| 2004/0211252 | A1* | 10/2004 | Lenormand | G01N 15/0826 73/152.05 |
| 2005/0189108 | A1 | 9/2005 | Davidson | |
| 2008/0162056 | A1* | 7/2008 | Greaves | E21B 43/006 702/24 |
| 2008/0216559 | A1* | 9/2008 | Hilab | E21B 25/005 73/38 |
| 2012/0223235 | A1 | 9/2012 | Maucec | |
| 2013/0054157 | A1* | 2/2013 | Lasseux | G01N 15/0826 702/47 |
| 2013/0144533 | A1* | 6/2013 | Kim | G01N 15/0806 702/12 |
| 2014/0366620 | A1* | 12/2014 | Haggerty | E21B 49/00 73/152.02 |
| 2015/0293007 | A1* | 10/2015 | Ramakrishnan | G01N 15/088 73/38 |
| 2015/0293008 | A1* | 10/2015 | Ramakrishnan | G01N 15/088 73/1.57 |
| 2015/0362419 | A1* | 12/2015 | Chertov | G01N 15/088 73/38 |
| 2015/0369718 | A1* | 12/2015 | Chertov | G01N 15/088 73/38 |
| 2015/0369719 | A1* | 12/2015 | Chertov | G01N 15/088 73/38 |

OTHER PUBLICATIONS

Allaire, G., "Homogenization of the Stokes flow in a Connected Porous Medium", Asymptotic Analysis, 1989, 2(3), pp. 203-222.
Biot, M. A., "Theory of Propagation of Elastic Waves in a Fluid-Saturated Porous Solid. I. Low-Frequency Range", The Journal of the Acoustical Society of America, 1956, 28(2), pp. 168-178.
Bourbie, T. et al., "Pulse Decay Permeability: Analytical Solution and Experimental Test", 1982, Stanford Rock Physics Project, Department of Geophysics, Stanford University, 11 pages.
Brace, W. F. et al., Permeability of Granite Under High Pressure, 1968, Journal of Geophysical Research, 73(6), pp. 2225-2236.
Cui, X. et al., "Measurements of gas permeability and diffusivity of tight reservoir rocks: different approaches and their applications", 2009, Geofluids, 9(3), pp. 208-223.
Cui, X. et al., "A New Method to Simultaneously Measure In-Situ Permeability and Porosity Under Reservoir Conditions: Implications for Characterization of Unconventional Gas Reservoirs", 2010, Canadian Society for Unconventional Gas, pp. 1-8.
Dicker, A. I. et al., "A Practical Approach for Determining Permeability From Laboratory Pressure-Pulse Decay Measurements", 1988, Society of Petroleum Engineers, pp. 285-292.
Dong, J. J. et al., "Stress-dependence of the permeability and porosity of sandstone and shale from TCDP Hole-A", International Journal of Rock Mechanics & Mining Sciences, 2010, 47, pp. 1141-1157.
Gong, X, et al., "Bayesian Probabilistic Decline-Curve Analysis Reliably Quantifies Uncertainty in Shale-Well-Production Forecasts", presented at the SPE Canadian Unconventional Resources Conference, Calgary, Canada, 2014, pp. 1047-1057.

Hsieh, P. A. et al., "A Transient Laboratory Method for Determining the Hydraulic Properties of 'Tight' Rocks—I. Theory", International Journal of Rock Mechanics and Mining Sciences and Geomechanics, 1981, 18(3): pp. 245-252.
Jannot, Y. et al., "A new quasi-steady method to measure gas permeability of weakly permeable porous media", Review of Scientific Instruments, 2012, 83(1), 13 pages.
Jones, S. C., "A Technique for Faster Pulse-Decay Permeability Measurements in Tight Rocks", 1997, SPE Formation Evaluation, pp. 19-25.
Kim, J. et al., "Novel Apparatus to Measure the Low-Permeability and Porosity in Tight and Shale Gas Reservoir", 2013, Proceedings of the 23rd International Offshore and Polar Engineering Conference, Anchorage, Alaksa, USA, pp. 61-67.
Neuzil, C. E., "A Transient Laboratory Method for Determining the Hydraulic Properties of 'Tight' Rocks—II. Application", 1981, International Journal of Rock Mechanics and Mining Sciences & Geomechanics Abstracts, 28, pp. 253-258.
Raghavan, R., "Well Test Analysis", 1993, PTR, Prentice-Hall, Inc. New Jersey, pp. 6-10.
Ramakrishnan, T. S. et al, "A Laboratory Investigation of Permeability in Hemispherical Flow with Application to Formation Testers", SPE Formation Evaluation, 1995, 10(2), pp. 99-108.
Recommended Practices for Core Analysis, Recommended Practice 40, Second Edition Feb. 1998, American Petroleum Institute, Section 6.1-6.57.
Rice, J. R. et al., "Some basic stress diffusion solutions for fluid-saturated elastic porous media with compressible constituents", Reviews of Geophysics, 1976, 14(2), pp. 227-241.
Sihna, S, et al., "Advances in Measurement Standards and Flow Properties Measurements for Tight Rocks such as Shales", SPE 152257, presented at the European Unconventional Resources Conference and Exhibition, Vienna, Austria, 2012, 13 pages.
Stadie, N. P. et al., Synthesis and Thermodynamic Studies of Physisorptive Energy Storage Materials, California Institute of Technology, 2013, 193 pages.
Search Report and Written Opinion of International Patent Application No. PCT/US2015/025542 dated Jul. 21, 2015, 10 pages.
Search Report and Written Opinion of International Patent Application No. PCT/US2015/025547 dated Jul. 6, 2015, 9 pages.
Detournay, et al., "Fundamentals of Poroelasticity," Comprehensive Rock Engineering-Principles, Practice and Projects, vol. 2, Analysis and Design Methods, J. A. Hudson, 1993, pp. 113-171.
Johnson, et al., ""New Pore-Size Parameter Characterizing Transport in Porous Media,", " Physical Review Letters, Nov. 17, 1986, vol. 57, No. 20, pp. 2564-2567.
Katz, et al., "Quantitative prediction of permeability in porous rock," Physical Review B, Dec. 1, 1986, vol. 34, No. 11, pp. 8179-8181.
Keller, "Darcy's law for flow in porous media and the two-space method," In: Nonlinear partial differential equations in engineering and applied science (Proc. Conf., Univ. Rhode Island, Kingston, RI, 1979), vol. 54. Dekker New York. 1980; pp. 429-443.
MacMullin, et al., "Characteristics of Porous Beds and Structures," AlChE Journal, 1956, vol. 2, No. 3, pp. 393-403.
Neuman, "Theoretical Derivation of Darcy's Law," Acta Mechanica, 1977, vol. 25, Issue 3-4, pp. 153-170.
Ramakrishnan, et al., "A Model-Based Interpretation Methodology for Evaluating Carbonate Reservoirs," SPE Annual Technical Conference and Exhibition, New Orleans, Louisiana, Sep. 30-Oct 3, 2001, SPE71704, pp. 1-15.
Sanchez-Palencia, "Homogenization in mechanics. a survey of solved and open problems," Rend Sem Mat Univers. Politecn. Torino. 1986, vol. 44, 1, pp. 1-45.
Slattery, "Single-phase flow through porous media," AlChE Journal, 1969, vol. 15, Issue 6, pp. 866-872.
Whitaker, "The method of volume averaging," Kluwer Academic, The Netherlands. 1998, pp. xi-xvi, 1-220.

* cited by examiner

METHOD FOR MEASUREMENT OF ULTRA-LOW PERMEABILITY AND POROSITY BY ACCOUNTING FOR ADSORPTION

RELATED APPLICATION

The present application claims the benefit of U.S. Provisional Application Ser. No. 62/159,750, filed on May 11, 2015, which is hereby incorporated by reference in its entirety.

The present application is related to U.S. application Ser. No. 14/252,599, filed on Apr. 14, 2014 and entitled "APPARATUS AND CALIBRATION METHOD FOR MEASUREMENT OF ULTRA-LOW PERMEABILITY AND POROSITY" and U.S. application Ser. No. 14/252,586, filed on Apr. 14, 2014 and entitled "METHODS FOR MEASUREMENT OF ULTRA-LOW PERMEABILITY AND POROSITY." Both of these applications are hereby incorporated by reference in their entireties.

BACKGROUND

1. Field

The subject disclosure relates to apparatus and methods for measuring the permeability and/or the porosity of a solid sample. The subject disclosure more particularly relates to apparatus and methods for measuring the permeability and/or porosity of a rock sample having an "ultra-low" permeability (in the range of hundreds of nanoDarcies to 100 milliDarcies) obtained from a geological formation, although it is not limited thereto.

2. State of the Art

For creeping incompressible fluid flow, with Reynolds number much less than unity, the Stokes equation in terms of microscopic velocity vector u is $$\partial_i P = \mu g_i + \partial_j \{\mu(\partial_j u_i + \partial_i u_j)\}, \quad (1)$$

where the subscripts i and j are cartesian component indices, $\rho$ is the density, P is the pressure, g is the gravitational acceleration, and $\mu$ is the shear or dynamic viscosity. For steady creeping flow in porous media, these equations scale up to macroscopic velocity components $$v_i = -\frac{\kappa}{\mu}(\partial_i P - \rho g_i), \quad (2)$$

where the fluid pressure P refers to a local volume average quantity in the Darcy formulation. This Darcy scaling is valid for a large range of pore sizes and velocities. As a consequence of the Stokes equation, the derivation of Darcy's law in the continuum form is shown to be valid through homogenization or local volume averaging.

It can be taken for granted that the validity of Darcy's law extends to slowly varying unsteady compressible flow. Accordingly, $v_i$ and P may vary with time, and for isothermal conditions $\rho$ may be evaluated from an explicit functional dependence on P. This approach, while prevalent, is often used without stating restrictions. For the approach to be valid, it is necessary that on the scale on which permeability is defined, variation in density should be negligible. The time-scale for external variation in fluxes or pressure should also be very large compared to the time scale for local establishment of Darcy's law.

Starting with Darcy's gravity-head based determination of proportionality between flux and pressure drop, experiments to determine permeability are well documented. It is assumed that for inert media, k is independent of the fluid, p being the normalizing factor containing the fluid property. Therefore, gas and liquid permeabilities are expected to be the same, unless the mean free path is comparable to pore size.

For gas permeability, a series of steady-state experiments relating flow-rate and pressure difference across the length L of the rock may be derived by combining continuity, equation of state, and Darcy's law. For an ideal gas, the result for isothermal flow is $$q_s = k \frac{(P_L^2 - P_R^2) A T_s}{2 T P_s \mu L} \quad (3)$$

where $P_L$ and $P_R$ are respectively the pressures on the "left" or upstream, and "right" or downstream sides of the rock, q is the flow rate, T is the temperature, and L is the length of the rock sample, A is the cross sectional area of the rock sample, with the subscript s referring to standard conditions. A series of appropriately chosen flow rates to stay within the optimal regime and the resulting steady-state pressure measurements allows for a determination of the permeability in a best-fit sense fairly accurately (see, e.g., U.S. Pat. No. 5,832,409 to Ramakrishnan et al.) The accuracy estimate using the steady-state method is better than 1 percent.

Two problems preclude the steady-state permeability measurement for rocks below about one mD. First, imposition of controllable or measurable flow rates results in excessive pressure drop, resulting in unknown nonlinear corrections. Second, the establishment of successive steady-states becomes onerously long, rendering the experiment impractical.

Analogous to well-testing pressure transient methods (see, e.g., Raghavan, R., *Well Test Analysis*, Prentice Hall, NJ (1993)), but in the laboratory, the transient build-up of pressure for an imposed flow-rate may be studied and the permeability inferred relatively quickly. Such methods are again error-prone because the build-up is affected by the line volumes, and the magnitude of the build-up needs to be determined a priori in order to reduce the nonlinear effects. It is the nonlinearity of both the rock behavior and the gas that precludes obtaining accurate transport properties with a step-rate method. For very low permeability rocks, the rates are too small to be measured reliably.

A concept for a system for measuring permeability of granites has been described by Grace et al., "Permeability of granite under high pressure," *J. Geophysical Res.*, 73 (6) 2225-2236 (1968). However, the analyses of Grace et al. do not take into account dead-volumes of the hardware in which the core is located, and the nonideality of the gas saturating the medium, and also do not provide a complete mathematical solution to the transient problem. As a result, the analyses of Grace et al. do not permit for accurate results.

Based on the methods of Grace et al., Hsieh et al., proposed a solution in terms of Laplace and inverse Laplace transforms. See, Hsieh et al., "A transient labaoratory method for determining the hydraulic properties of 'tight' rocks," *Int. J. Rock Mech. Min. Sci. and Geomech*, 18, 245-252, 253-258 (1981). The analysis of Hsieh et al., however, does not include nonideality of the gas explicitly and its influence of the transient characteristics. Dead-volume connected to the core is also not included. Interpretation is based on what Hsieh et al. call as an early-time semi-infinite solution or the late-time single exponential result. Hsieh et al. analyze upstream and downstream pressures or their difference with respect to the final pressure. As a result, the solution of Hsieh et al., does not permit for accurate results.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Various embodiments of the present disclosure are directed to a method of characterizing permeability of a sample located in a sample chamber. The method includes: (a) causing a sample chamber pressure and an upstream and downstream pressure to be the same; (b) increasing the upstream pressure by a perturbation percentage while holding the sample chamber and downstream pressures constant; (c) monitoring the upstream and downstream pressures as a function of time while permitting the sample chamber pressure and the upstream and downstream pressures to start equilibrating; (d) finding a decay constant relating to the difference in the measured upstream and downstream pressures over time; and (e) utilizing the decay constant to generate a permeability estimate of the sample by accounting for adsorption of gas within the sample.

Illustrative embodiments of the present disclosure are also directed to a method of characterizing permeability of a sample located in a sample chamber. The method includes: (a) causing a sample chamber pressure and an upstream and downstream pressure to be the same; (b) causing a pressure perturbation so that the downstream pressure is lower than at least one of the upstream pressure and the sample chamber pressure; (c) monitoring the downstream pressure as a function of time while permitting the upstream and downstream pressures to start equilibrating; (d) finding a peak value time of a derivative of the downstream pressure signal; and (e) using the peak value time to find a permeability estimate of the sample by accounting for adsorption of gas within the sample.

Various embodiments of the present disclosure are directed to a method of characterizing porosity of a sample located in a sample chamber. The method includes: (a) causing a sample chamber pressure and an upstream and downstream pressure to be the same; (b) increasing the upstream pressure by a perturbation percentage while holding the sample chamber and downstream pressures constant; (c) monitoring the upstream and downstream pressures as a function of time while permitting the sample chamber pressure and the upstream and downstream pressures to start equilibrating; and (d) estimating the porosity $\phi$ according to the relationship $\phi = 4V_c/(LA)$, where $V_c$ is determined according to the relationship:

$$V_c = V_L \frac{\left(\frac{P_f}{Z_f} - \frac{V_l}{V_L}\frac{P_{l0}}{Z_{l0}} - \frac{V_h}{V_L}\frac{P_{R0}}{Z_{R0}}\right)}{\left(\frac{P_{R0}}{Z_{R0}} - \frac{P_f}{Z_f} + c_\eta(P_{R0} - P_f)\right)} - V_R \frac{\left(\frac{P_{R0}}{Z_{R0}} - \frac{P_f}{Z_f}\right)}{\left(\frac{P_{R0}}{Z_{R0}} - \frac{P_f}{Z_f} + c_\eta(P_{R0} - P_f)\right)},$$

where L and A are the length and cross-sectional area of the sample respectively, $V_L$ is a total volume upstream of the sample chamber, $V_R$ is a total volume downstream of the sample chamber, $P_f$ is an equilibrated pressure, $P_{R0}$ is the downstream pressure prior to a start of the equilibrating, $P_{l0}$ is the upstream pressure prior to a start of the equilibrating, $V_l$ is a calibrated volume of an upstream chamber, $V_h$ is a connection volume between the sample chamber and an upstream valve between the sample chamber and the upstream chamber, $c_\eta$ is a quasi-linear adsorption coefficient, and $Z_{l0}$, $Z_{R0}$, and $Z_f$ are compressibility factors.

DETAILED DESCRIPTION

It should be noted at the outset that in the summary and this detailed description, each numerical value should be read once as modified by the term "about" (unless already expressly so modified), and then read again as not so modified unless otherwise indicated in context. Also, in the summary and this detailed description, it should be understood that a concentration range listed or described as being useful, suitable, or the like, is intended that any and every concentration within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific, it is to be understood that inventors appreciate and understand that any and all data points within the range are to be considered to have been specified, and that inventors possessed knowledge of the entire range and all points within the range.

Figure 1A:
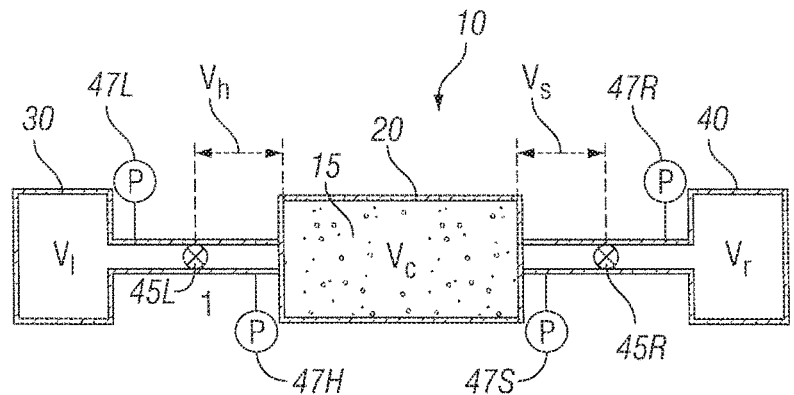
FIG. 1A is a schematic of one embodiment of an apparatus useful in measuring permeability and/or porosity of a solid sample.

Turning to FIG. 1A, a high-level schematic of an apparatus 10 useful for measuring the permeability and/or porosity of a low permeability sample 15 is seen. Apparatus 10 includes sample chamber 20 (discussed in more detail hereinafter) for a sample 15 (such as a formation core), an upstream or "left" chamber 30, and a downstream or "right" chamber 40.

In various embodiments, the sample chamber 20 supports a sample 15 having a length (L) and a cross-sectional area (A). For example, the sample 15 may be a core sample with a cylindrical shape with a length (L) and a circular cross-section having a diameter (D). In other embodiments, the sample chamber 20 supports a sample 15 having an ellipsoidal cross-section.

Valves 45L and 45R are optionally remotely controlled solenoid valves and are located respectively between the left chamber 30 and the sample chamber 20, and between the sample chamber 20 and the right chamber 40. The volume between the valve and the sample chamber on the left side is denoted as $V_h$, and similarly the volume between the valve and the sample chamber on the right side is denoted $V_s$. The volumes of chambers 30 and 40 are denoted $V_l$ and $V_h$ respectively. Thus, valves 45L and 45R separate $V_l$ and $V_h$, and $V_r$ and $V_s$, respectively. Two or more pressure sensors are provided for sensing the pressure upstream and downstream of the sample chamber. In FIG. 1A, four pressure sensors 47L, 47H, 47S, and 47R are shown and sense the pressure at the upstream chamber 30, the upstream side of the sample chamber 20, the downstream side of the sample chamber 20 and the downstream chamber 40 respectively. As will be described hereinafter, in one embodiment, an apparatus for pressurizing (i.e., pressure charging) the apparatus 10 is coupled to the upstream chamber 30. Also as described hereinafter, in one embodiment a sequence of chambers may be connected to the upstream chamber 30 and/or the downstream chamber 40 so that by actuating different valves, the left and right volumes may be chosen before commencing an experiment. Ports to facilitate automated calibration, and multiple solenoids are also described hereinafter.

In one embodiment, a chamber of volume $V_l$ is connected to a line of volume $V_h$ via a solenoid 45L that operates almost instantly. Various volumes for $V_l$ may be used. The total volume upstream of the sample chamber may then be written as $$V_L = V_l + V_h \quad (4)$$

Similarly, a second chamber of volume $V_r$ and a line of volume $V_s$ separated from each other by solenoid 45R is connected to the downstream side of the sample chamber. Various volumes for $V_r$ may be used. The total volume downstream of the sample chamber may be expressed as:

$$V_R = V_r + V_s \quad (5)$$

For t<0 (before the beginning of the experiment), the left and right chambers are kept at pressures $P_{l0} = P_l(0)$ and $P_{r0} = P_r(0)$ respectively. The left solenoid 45L is in a closed state. By design, by keeping the right solenoid 45R open, the volumes $V_h$, and $V_s$ and the core sample whose pore volume is denoted as $V_c$ are kept at pressure $P_{r0}$ as well.

At time t=0 (the start of the experiment), the left solenoid is opened, and the left and right pressures, $P_l(t)$ and $P_r(t)$, in volumes $V_l$ and $V_r$ respectively, are recorded by absolutely and relatively calibrated transducers 47L and 47R. In one embodiment, relative calibration is important because interpretation is based on the signal difference $P_l(t) - P_r(t)$ as is discussed hereinafter.

Since the permeability of the core is finite and there is little resistance to flow between $V_l$ and $V_h$, upon opening the left solenoid 47L, nearly instantaneous pressure equilibration can be assumed in the left side. This equilibrated pressure is given by $P_{L0} = P_L(0)$. On the right hand side, before any flux is seen by the core, the pressure $P_{r0}$ is the same as the pressure within the core and the volume $V_s$. For consistency in notation, this pressure is denoted $P_{R0}$. With density subscripts similar to that of pressure, $P_{L0}$ is calculated from mass conservation $$V_l \rho_{l0} + V_h \rho_{h0} = V_L \rho_{L0}, \quad (6)$$

and an equation of state for density at temperature T, $$\rho = \frac{PM}{RTZ(P)}, \quad (7)$$

where R is the gas constant, M is the molecular weight of the gas, and Z is the compressibility factor which is a function of pressure. Since the analysis is for a fixed temperature, the dependency of compressibility factor on T is not of concern here. Thus, with $Z_{l0} = Z(P_{l0})$, $Z_{L0} = Z(P_{L0})$, and $Z_{R0} = Z(P_{R0})$, the following is obtained:

$$\rho_{l0} = \frac{P_{l0} M}{RTZ_{l0}}; \rho_{L0} = \frac{P_{L0} M}{RTZ_{L0}}; \text{ and } \rho_{R0} = \frac{P_{R0} M}{RTZ_{R0}}, \quad (8)$$

so that density may be computed on the left side of the core at t=0 from $$\rho_{L0} = \frac{1}{V_l + V_h}(V_l \rho_{l0} + V_h \rho_{R0}), \quad (9)$$

and $P_{L0}$ may be obtained from the middle expression in equation (8). In accordance with the above nomenclature, $$P_{L0} = \frac{V_l}{V_L} \frac{Z_{L0}}{Z_{l0}} P_{l0} + \frac{V_h}{V_L} \frac{Z_{L0}}{Z_{R0}} P_{R0}, \quad (10)$$

which is an expression that can be solved iteratively. Thus $\rho_{L0}$, $\rho_{R0}$, $P_{L0}$ and $P_{R0}$ are known. It should also be noted that for interpretation purposes, for t>0, $P_L(t) = P_l(t)$ and $P_R(t) = P_r(t)$.

In one embodiment, prior calibration of the chamber volumes is desirable. As previously described, apparatus 10 includes an arrangement of valves related to pressure taps and transducers, and multiple volume chambers. These make the determination of $V_l$, $V_r$, $V_L = V_l + V_h$, and $V_R = V_r + V_s$ non-trivial.

Considering the schematic of the experiment shown in FIG. 1A, a series of ten experiments were performed that in the least square sense allows for a solution for the four volumes $V_l$, $V_h$, $V_s$ and $V_r$. The first experiment starts with pressure $P_l$ in $V_l$ and a slightly lower pressure in $V_h$ at $P_h$. $V_h$ is isolated from the right side by using a solid metal cylinder instead of a low permeability sample in or as the sample chamber 20. Upon opening the valve in-between and waiting, the final pressure in the first experiment is $P_f$. Then $$\frac{P_f(V_l + V_h)}{Z_f RT} = \frac{P_l V_l}{Z_l RT} + \frac{P_h V_h}{Z_h RT}, \quad (10A)$$

where Z's subscript corresponds to the appropriate pressure with the same subscript. Defining $x_{lh}$ as follows, the following is obtained $$x_{lh} := \frac{V_l}{V_l + V_h} = \left(\frac{P_f}{Z_f} - \frac{P_h}{Z_h}\right) \bigg/ \left(\frac{P_l}{Z_l} - \frac{P_h}{Z_h}\right). \quad (10B)$$

The numerical value of $x_{lh}$ is known from the first experiment since all quantities on the right hand side of equation (10B) are obtained from the measured pressures.

A second experiment involves a change from the first experiment in that a metallic cylinder of bore with volume $V_{c1}$ replaces the solid cylinder as the sample chamber. The valve 45R is kept shut throughout, but valve 45L is opened to equilibrate pressure in $V_l$ and $V_h + V_{c1} + V_s$. With the initial pressure on the right side being $P_{h1s}$, the other notations being self-evident, an equation similar to equation (5) is generated:

$$x_{lh1s} := \frac{V_l}{V_l + V_h + V_{c1} + V_s} = \left(\frac{P_f}{Z_f} - \frac{P_{h1s}}{Z_{h1s}}\right) \bigg/ \left(\frac{P_l}{Z_l} - \frac{P_{h1s}}{Z_{h1s}}\right). \quad (10C)$$

In a third experiment, the hollowed cylinder has a volume $V_{c2}$ rather than $V_{c1}$. A sufficient difference between $V_{c2}$ and $V_{c1}$ is allowed in order to provide the necessary resolution for inferring the volumes. For the third experiment, analogous to the second experiment:

$$x_{lh2s} := \frac{V_l}{V_l + V_h + V_{c2} + V_s} = \left(\frac{P_f}{Z_f} - \frac{P_{h2s}}{Z_{h2s}}\right) \bigg/ \left(\frac{P_l}{Z_l} - \frac{P_{h2s}}{Z_{h2s}}\right). \quad (10D)$$

The fourth, fifth, and the sixth experiments are repetitions of the first three but on the right hand side. With the subscript r replacing l in the previous equations, $$x_{rs} := \frac{V_r}{V_r + V_s} = \left(\frac{P_f}{Z_f} - \frac{P_s}{Z_s}\right) \bigg/ \left(\frac{P_r}{Z_r} - \frac{P_s}{Z_s}\right), \quad (10E)$$

$$x_{rs1h} := \frac{V_r}{V_l + V_s + V_{c1} + V_h} = \left(\frac{P_f}{Z_f} - \frac{P_{s1h}}{Z_{s1h}}\right) \bigg/ \left(\frac{P_r}{Z_r} - \frac{P_{s1h}}{Z_{s1h}}\right), \quad (10F)$$

and $$x_{rs2h} := \frac{V_r}{V_l + V_s + V_{c2} + V_h} = \left(\frac{P_f}{Z_f} - \frac{P_{s2h}}{Z_{s2h}}\right) \bigg/ \left(\frac{P_r}{Z_r} - \frac{P_{s2h}}{Z_{s2h}}\right). \quad (10G)$$

The seventh and the eighth experiments repeat the second and the third experiments, but with the valve 45R opened as well, so that the entire system has the same final pressure. The initial higher pressure is in volume $V_l$ alone. With $V_{1t} = V_l + V_h$ $+ V_{c1} + V_s + V_r$ and $V_{2t} = V_l + V_h + V_{c2} + V_s + V_r,$ $$x_{l1t} := \frac{V_l}{V_{1t}} = \left(\frac{P_f}{Z_f} - \frac{P_R}{Z_R}\right) \bigg/ \left(\frac{P_l}{Z_l} - \frac{P_R}{Z_R}\right) \text{ and} \quad (10H)$$

$$x_{l2t} := \frac{V_l}{V_{2t}} = \left(\frac{P_f}{Z_f} - \frac{P_R}{Z_R}\right) \bigg/ \left(\frac{P_l}{Z_l} - \frac{P_R}{Z_R}\right) \quad (10I)$$

Note that the subscript R for P and Z indicate that the initial low pressure side includes $V_s$, $V_c$, $V_h$ and $V_r$. In order not to proliferate the number of symbols, subscripts 1 and 2 have not been used to denote pressures and compressibilities.

Another set of two experiments repeat the seventh and the eighth experiments, except that the initial high pressure is in volume $V_r$ (chamber 40). With a notation for the right corresponding to those introduced in the previous two equations, $$x_{r1t} := \frac{V_r}{V_{1t}} = \left(\frac{P_f}{Z_f} - \frac{P_L}{Z_L}\right) \bigg/ \left(\frac{P_r}{Z_r} - \frac{P_L}{Z_L}\right) \text{ and} \quad (10J)$$

$$x_{r2t} := \frac{V_r}{V_{2t}} = \left(\frac{P_f}{Z_f} - \frac{P_L}{Z_L}\right) \bigg/ \left(\frac{P_r}{Z_r} - \frac{P_L}{Z_L}\right).$$

It is convenient to represent these equations as $$\begin{bmatrix} (1-x_{lh}) & -x_{lh} & 0 & 0 \\ (1-x_{lh1s}) & -x_{lh1s} & -x_{lh1s} & 0 \\ (1-x_{lh2s}) & -x_{lh2s} & -x_{lh2s} & 0 \\ 0 & 0 & -x_{rs} & 1-x_{rs} \\ 0 & -x_{rs1h} & -x_{rs1h} & 1-x_{rs1h} \\ 0 & -x_{rs2h} & -x_{rs2h} & 1-x_{rs2h} \\ (1-x_{l1t}) & -x_{l1t} & -x_{l1t} & -x_{l1t} \\ (1-x_{l2t}) & -x_{l2t} & -x_{l2t} & -x_{l2t} \\ -x_{r1t} & -x_{r1t} & -x_{r1t} & (1-x_{r1t}) \\ -x_{r2t} & -x_{r2t} & -x_{r2t} & (1-x_{r2t}) \end{bmatrix} \begin{bmatrix} V_l \\ V_h \\ V_s \\ V_r \end{bmatrix} = \begin{bmatrix} 0 \\ x_{lh1s} V_{c1} \\ x_{lh2s} V_{c2} \\ 0 \\ x_{rs1h} V_{c1} \\ x_{rs2h} V_{c2} \\ x_{l1t} V_{c1} \\ x_{l2t} V_{c2} \\ x_{r1t} V_{c1} \\ x_{r2t} V_{c2} \end{bmatrix}. \quad (10K)$$

Represented in matrix notation the corresponding equation is $$XV = M \quad (10L)$$

where X is a 10×4 matrix, V is the column vector of four unknown volumes, and M is the column vector of the product of the ten measurements and known bore-volumes from the metal cylinders. The volume vector in the least square sense is explicitly arrived at in terms of the generalized inverse, whereby $$V = (X^T X)^{-1} X^T M \quad (10M)$$

with superscript T indicating matrix transpose.

Several alternative volumes $V_l$ and $V_r$ may be chosen for resolvable pressure decay, and these experiments are repeated for each such left and right volume pairs. Since $V_h$ and V are common for all such sequences, a consistency check is automatically obtained.

For each experiment, at least some of the solenoid valves are first kept open for initializing the pressure. By choice, this pressure is the lower of the two. In the open state the valves are also charged to the lower pressure. The valves separating the lower and higher pressure are closed before charging the high pressure volume. For equilibration, the valve is opened again, and the low pressure charge of the valve comes back into communication. A small error is introduced in the process, much of which may be negated by including the valve volume as an unknown, and inverting for it from the expanded form of equation (10K). Generally, this may be considered a nonissue.

Once the volumes are measured, they are a part of the specification for the apparatus for the same core length. In one embodiment, any minor variations in the core length may be considered to have no material consequence to the final interpretation of permeability since it affects $V_L$ and $V_R$ negligibly and therefore does little to change $\alpha_L$ and $\alpha_R$ (the ratios of the pore volume of the core to the upstream and downstream volumes as discussed hereinafter). However, by placing the core symmetrically, the change to $V_L$ and $V_R$ is easily calculated and accommodated for inferring porosity (as discussed hereinafter). In one embodiment, for extremely low permeability samples (sub-microDarcy), in order to keep equilibration time to a reasonable length, shorter core lengths are preferable. Since the core holder can be designed for a specific core length, the shorter core can be sandwiched between metallic sleeves, thus introducing additional dead volumes to $V_h$ and $V_s$. These additional volumes are known from the geometry of the sleeves.

According to one aspect, it can be quite difficult to measure small differential pressures accurately for large absolute pressures. In addition, any measurement system, especially those for differential pressures, affect the measurement itself through membrane deflection. In one embodiment, high-accuracy (better than 0.1% class and hand-selected) absolute transducers are used, with deliberate adjustment of range and accuracy cross-calibration during the experimental procedure. For primary calibration, in one embodiment, a dead-weight tester is used. For routine checks, a NIST (National Institute of Standards and Technology) and traceable secondary calibrator is used.

Elimination of offset allows the accuracy of interpretation to be improved substantially, and also provides means to infer porosity as described hereinafter. As also described hereinafter, the porosity may be used as a consistency check for the permeability determination, especially when the core porosity is greater than 0.10.

Prior to running experiments, a set of stress values and gas pressures are selected. The sequence of stresses and pressures is carefully chosen. At each desired gas pressure of the experiment (nominally $P_f$), $P_{l0}$ and $P_{r0}$ are chosen. For each of the experiments the offset between the transducers is calculated when $P_{r0}$ is set on the left and the right sides, prior to shutting valve 45L and elevating pressure $P_{r0}$ to $P_{l0}$ on the left side.

For precise cross-calibration, a range off-set can also be useful. The same procedure may be carried out at $P_{l0}$ and $P_{r0}$ and then the right side may be bled down to $P_{r0}$ to get two-offsets at $P_{l0}$ and $P_{r0}$ before commencing the transient pressure decay experiment. If the measured cross-calibration pressures are denoted by a parenthetic superscript of l or r that refers to the transducer, and the mean pressure between the two is used as the reference pressure, then the corrected pressure for the left and right sides are $$P_l = \left[\frac{(P_{lo}^{(l)} + P_{lo}^{(r)}) - (P_{ro}^{(l)} + P_{ro}^{(r)})}{2(P_{lo}^{(l)} - P_{ro}^{(l)})}\right]\{P^{(l)} - P_{ro}^{(l)}\} + \frac{P_{ro}^{(l)} + P_{ro}^{(r)}}{2} \quad (10N)$$

and $$P_r = \left[\frac{(P_{lo}^{(l)} + P_{lo}^{(r)}) - (P_{ro}^{(l)} + P_{ro}^{(r)})}{2(P_{lo}^{(r)} - P_{ro}^{(r)})}\right]\{P^{(r)} - P_{ro}^{(r)}\} + \frac{P_{ro}^{(l)} + P_{ro}^{(r)}}{2}. \quad (10O)$$

These equations are sufficient to correct for small discrepancies that are common between two absolute pressure transducers.

Turning now to a discussion of pressure perturbation, without loss of generality, let $P_{L0} > P_{R0}$. In one embodiment, in conducting an experiment, it is desirable for $P_{L0} - P_{R0} \ll P_{R0}$. For perturbation accuracy, a reference quiescent state can be chosen based on the final pressure $P_f$, which is $P_L(t \to \infty)$ and $P_R(t \to \infty)$. The pressure in the core is P and varies with time and with the distance x measured, e.g., from the face of the sample exposed to $P_L$. A perturbed dimensionless pressure is now defined by $$v(\xi, \tau) = -1 + \frac{P(x, \tau)}{P_f} \quad (11)$$

or $$P = P_f(1 + v)$$

where the dimensionless distance $\xi$ and dimensionless time $\tau$ are yet to be defined in terms of x and t respectively, and the arguments for P and v are implied. Given the restriction on $P_L(t) - P_R(t)$, it is seen that $v \ll 1 \forall x$ and t. Consistent with the notation introduced thus far, the dimensionless perturbed pressure v for the initial state becomes $$v_{l0} = -1 + \frac{P_{l0}}{P_f}; \quad (12)$$

$$v_{L0} = -1 + \frac{P_{L0}}{P_f};$$

and $$v_{R0} = -1 + \frac{P_{R0}}{P_f}.$$

Although $v(\xi, \tau)$ is a dependent variable for the pressure transient problem, for the equation of state, and for constructing the differential equation, v is regarded as a perturbation quantity. Formally, v would be scaled with respect to a small parameter $(P_{L0} - P_{R0})/P_f$ to keep it on the order of unity (i.e., $O(1)$), and the small parameter would be used for a perturbation expansion. However, in one embodiment this is unnecessary for a leading order analysis if it is realized that $v(\xi, \tau) \ll 1$.

Turning now to a discussion of the nonideality in gas flow, in order to retain the leading order terms due to gas nonideality, the compressibility factor is expanded as $$Z(P) = Z(P_f(1+v)) = Z(P_f) + vP_f Z'(P_f) + \ldots = Z_f + vP_f Z'_f + \ldots \quad (13)$$

where $Z_f = Z(P_f)$ and $Z'_f = dZ(P_f)/dP$. By the principle of corresponding states and the use of acentric factor, $\omega$, $$Z(P) = Z^{(r)}(P_r) = Z^0(P_r) + \omega Z^{(1)}(P_r) \quad (14)$$

where $P_r$ is the reduced pressure, $Z^{(r)}(P_r) = O(1)$ and $dZ^{(r)}/(dP_r) = O(1)$ with the notation that $$Z_f^{(r)} = Z^{(r)}\left(\frac{P_f}{P_c}\right)$$

and $$Z'^{(r)}_f = \frac{dZ_f^{(r)}}{dP_r}$$

at $$P_f / P_c,$$

$$Z'_f = Z'^{(r)}_f / P_c.$$

Then the compressibility factor may be expanded in terms of v so that $$Z(P) = Z_f(1 + v\gamma Z'^{(r)}_f) \quad (15)$$

where $\gamma = P_f/(P_c Z_f)$ and is $O(1)$. The implication of equation (15) is that the leading order compressibility factor is $Z_f$ with a correction factor of order $v$. As is explained hereinafter, the ratio $P/Z(P)$ appears in the governing equation. The perturbation expansion for $P/Z(P)$ is $$\frac{P}{Z(P)} = \frac{P_f}{Z_f}(1 + v(1 - \gamma Z_f'^{(r)}) + \ldots). \quad (16)$$

For compactness of terms in equation (16), the following notation may be used:

$$G_f = (1 - \gamma Z_f'^{(r)}), \quad (17)$$

$$E_f = \frac{P_f}{Z_f},$$

so that $$\frac{P}{Z(P)} = E_f(1 + vG_f + \ldots).$$

NIST quoted values of density in the temperature range 290-300 K have been used. More particularly, NIST data on density over the cited temperature range has been used to compute $Z(P)$ and represent it as Padé approximant $$Z(P; T) = \frac{1 + a_{1z}(T)P + a_{2z}(T)P^2 + \ldots}{1 + b_{1z}(T)P + b_{2z}(T)P^2 + \ldots}. \quad (17A)$$

Having computed the coefficients at a number of temperatures, a Padé approximant may be constructed for the coefficients as well. It can be seen that over the limited temperature range of 10 Kelvin, a quadratic approximation for temperature dependence was appropriate. By limiting the uncertainty in the coefficients of the quadratics, it may be inferred that it is preferable to make coefficients higher than $a_{2z}$ and $b_{1z}$ equal to zero. $Z'(P)$ is computed from the analytical derivative of equation (17A).

For viscosity, a good approximation is obtained in the range of interest with $$\mu(P; T) \approx \frac{a_{0\mu} + a_{1\mu}P}{1 + b_{1\mu}P} \quad (17B)$$

where the Padé coefficients are expressed as linear functions of temperature.

Differential equations may be written that are relevant to pressure decay. Although the problem is one-dimensional, for consistency, the superficial velocity in the direction x is denoted $v_x$. The mobility denoted $\lambda$ is $k/\mu$, where $\mu$ is the viscosity of the gas used in the experiment, and the mobility is a function of pressure for a given stress. Then, $$v_x = \lambda \frac{\partial P}{\partial x}, \quad (18)$$

where gravity terms have been dropped. Gas continuity gives $$\phi \frac{\partial \rho}{\partial t} + \frac{\partial \rho v_x}{\partial x} = 0. \quad (19)$$

Substituting for density with equation (7), and utilizing equation (17), the governing differential equation in terms of $v$ becomes $$\frac{\partial v}{\partial t} - \frac{\lambda_f}{\phi}(1 + vG_f)\frac{P_f}{G_f}\frac{\partial^2 v}{\partial x^2} - \frac{\lambda_f}{\phi}P_f\left(\frac{\partial v}{\partial x}\right)^2 + o(v) = 0 \quad (20)$$

where $o$ indicates that as $v$ goes to zero, whatever term is divided by $v$ goes to zero, and where $\lambda_f = \lambda(P_f; \sigma)$. Here the mean stress $\sigma$ has been regarded as a parameter. With $\rho_L$ as the density in the left chamber, mass conservation gives $$V_L \frac{d\rho_L}{dt} = -A\rho_L v_x(0, t). \quad (21)$$

A similar result for the right chamber with gas density $\rho_R$ is $$V_R \frac{d\rho_R}{dt} = A\rho_R v_x(1, t). \quad (22)$$

In one aspect, a nondimensional formulation may be generated. With a natural length scale L and the dimensionless distance $\xi = x/L$, the time scale $T_T$ is chosen to be $$T_T = \frac{\phi L^2 G_f}{\lambda_f P_f} \quad (23)$$

which then gives (from equation (20)), $$\frac{\partial v}{\partial \tau} = \frac{\partial^2 v}{\partial \xi^2} + \ldots, \quad (24)$$

where $\tau = t/T_T$. Replacing $\rho_L$ in terms of $P_L$ from equation (7), using $v_L = -1 + P_L/P_f$, and replacing $P/Z(P)$ ratios from equation (17), the dimensionless form of equation (21) is obtained:

$$\frac{dv_L(\tau)}{d\tau} = \alpha_L \frac{\partial v(0, \tau)}{\partial \xi} + \ldots \quad (25)$$

Note that $v_L(T) = v(0, \tau)$, and $$\alpha_L = \frac{V_c}{V_L} \quad (26)$$

With $v_R(t) = v(1, \tau)$, a similar equation for the right side from equation (22) is obtained:

$$\frac{dv_R(\tau)}{d\tau} = -\alpha_R \frac{\partial v(1, \tau)}{\partial \xi} + \ldots \quad (27)$$

where $\alpha_R = V_c/V_R$. Equations (24), (25) and (27) are solved together with the initial condition $$v(\xi, 0) = \begin{cases} v_{L0}, & \xi = 0 \\ v_{R0}, & 0 < \xi \le 1 \end{cases} \quad (28)$$

The above problem posed by equation (24) and the initial and boundary conditions may be solved by Laplace transforms. A more direct and explicit method of solving equation (24) is through separation of $\tau$ and $\xi$. However, as illustrated below, the eigenfunctions will be non-orthogonal since the boundary conditions have time derivatives.

Turning now to a time domain solution, to begin with, a solution in the form of $$v(\xi,\tau) = \chi(\xi)Y(\tau), \quad (29)$$

is sought, which from equation (24) gives $$\chi''(\xi) + \beta^2 \chi(\xi) = 0, \text{ and } \dot{Y}(\tau) + \beta^2 Y = 0, \quad (30)$$

where the $'$ and accents represent the derivative with respect to the argument variable, and $\beta$ is the eigenvalue. As is described hereinafter, there are infinite values of $\beta$ that are possible. Therefore, together with the boundary condition at $\xi=0$ and $\xi=1$, $$v(\xi, \tau) = \sum_{1} A_n e^{-\beta_n^2 \tau} \left[ \sin(\beta_n \xi) - \frac{\alpha_L}{\beta_n} \cos(\beta_n \xi) \right] \quad (31)$$

is obtained where $A_n$ are constants and $\beta_n$ satisfy the transcendental expression $$\frac{\beta_n(\alpha_L + \alpha_R)}{\beta_n^2 - \alpha_L \alpha_R} = \tan\beta_n \quad (32)$$

For compactness, the definition $$H_n(\xi) := \sin(\beta_n \xi) - \frac{\alpha_L}{\beta_n} \cos(\beta_n \xi) \quad (33)$$

is used which satisfy (see equation (30))

$$H''_n + \beta_n^2 H_n = 0. \quad (34)$$

Repeating this for another index m, multiplying each with $H_m$ and $H_n$ respectively, and subtracting, $$(H_m H'_n - H_n H'_m)' + (\beta_n^2 - \beta_m^2) H_n H_m = 0 \quad (35)$$

is obtained. When integrated with respect to $\xi$, and combined with $\xi=0$ and $\xi=1$ boundary conditions, the above equation leads to the extended orthogonality result that for $n \ne m$, $$\int_0^1 H_m(\xi) H_n(\xi) d\xi = -\frac{1}{\alpha_R} H_m(1) H_n(1) - \frac{1}{\alpha_L} H_m(0) H_n(0) \quad (36)$$

In one aspect, it has been shown that the time dependent boundary condition leads to nonorthogonal eigenmodes. To solve for $A_n$, the modal amplitudes, $v$ is first written in terms of $H_n$, $$v(\xi,\tau) = \Sigma_{n=1} A_n e^{-\beta_n^2 \tau} H_n(\xi) \quad (37)$$

so that $$v_{L0} = \Sigma_{n=1} A_n H_n(0) \quad (38)$$

and $$v_{R0} = \Sigma_{n=1} A_n H_n(1) \quad (39)$$

Using the notation $v_0(\xi) = v(\xi, 0)$, and the initial profile based on equations (28) and (37), the product $$v_0(\xi) H_m(\xi) = \Sigma_1 A_n H_n(\xi) H_m(\xi) \quad (40)$$

when integrated with respect to $\xi$ becomes $$v_{R0} \int_0^1 H_m(\xi) d\xi = \Sigma_{n=1} A_n \int_0^1 H_n(\xi) H_m(\xi) d\xi \quad (41)$$

Equations (38) and (39) are now multiplied by (0) and (1) respectively, and equation (41) is added, and the extended orthogonality result of equation (36) is utilized to obtain $$A_n = \frac{v_{R0} \int_0^1 H_n(\xi) d\xi + \frac{v_{L0}}{\alpha_L} H_n(0) + \frac{v_{R0}}{\alpha_R} H_n(1)}{\int_0^1 H_n^2 d\xi + \frac{H_n^2(0)}{\alpha_L} + \frac{H_n^2(1)}{\alpha_R}} \quad (42)$$

For completeness, it is noted that $$\int_0^1 H_n(\xi) d\xi = \frac{1}{\beta_n^2} \{-\alpha_L \sin\beta_n + \beta_n(1 - \cos\beta_n)\}, \text{ and} \quad (43)$$

$$\int_0^1 H_n^2(\xi) d\xi = \quad (44)$$
$$\frac{-4\alpha_L \beta_n \sin^2 \beta_n - \beta_n^2 \sin 2\beta_n + 2\beta_n^3}{4\beta_n^3} + \frac{\alpha_L^2 \sin 2\beta_n + 2\alpha_L^2 \beta_n}{4\beta_n^3}$$

It might be perceived that the first eigenvalue $\beta_1$ is the most relevant, since within a short time the remaining eigenmodes become negligible. Experimentally, however, in one embodiment it is desirable to utilize the data from early times, and terminate the experiment as soon as a satisfactory calculation for permeability is obtained. To ensure sufficiency of retaining just the leading mode in interpreting the pressure equilibration requires appropriate apparatus design for which it is useful to study the amplitudes $A_n$ with respect to parameters $\alpha_L$ and $\alpha_R$. In one embodiment, a proposed design aims for a better than one percent accuracy for the amplitude with the very first eigenmode. This may be accomplished by allowing up to 75 mL for $V_L$ and $V_R$. The larger volumes are needed when $\phi \ge 0.25$. For lower porosity and certain ultralow permeability samples, e.g., below 100 µD, there is flexibility to reduce this volume down to 10 mL each (as discussed hereinafter). Naturally then, for real-time calculation, explicit algebraic expressions for the leading mode may be desirable.

Four separate cases for $\beta_1$ are available. In the first case, $\alpha_L \alpha_R < \pi^2/4$; the second case is when $\alpha_L \alpha_R = \pi^2/4$, for which $\beta_1 = \pi/2$; and the third case occurs when $\alpha_L \alpha_R > \pi^2/4$, but is less than $\pi^2$. The fourth case occurs when $\alpha_L \alpha_R > \pi^2$. In practice, $\alpha_L$ and $\alpha_R \ll 1$, which implies the first case. An excellent approximation to $\beta_1$ may then be obtained. For this purpose let $$\epsilon := \alpha_L \text{ and } \alpha := \alpha_R/\epsilon, \qquad (45)$$

where, by design, $\alpha$ is of order unity. Now consider the ansatz $$\beta_1 = \sqrt{\epsilon}(\beta_{10} + \epsilon\beta_{11} + \epsilon^2\beta_{12} + \epsilon^3\beta_{13} + \ldots). \qquad (46)$$

This series may be inferred by starting with an arbitrary gauge function based expansion, and imposing internal consistency. Substituting equation (46) in equation (32) and matching terms of the same order, the following results correct to order $\epsilon^{7/2}$ are obtained:

$$\beta_{10} = \sqrt{1+\alpha}, \qquad (47)$$

$$\beta_{11} = \frac{-1+\alpha-\alpha^2}{6\sqrt{1+\alpha}}, \qquad (48)$$

$$\beta_{12} = \frac{11+14\alpha-39\alpha^2+14\alpha^3+11\alpha^4}{360(1+\alpha)^{3/2}}, \text{ and} \qquad (49)$$

$$\beta_{13} = \frac{-17-81\alpha-66\alpha^2+311\alpha^3-66\alpha^4-81\alpha^5-17\alpha^6}{5040(1+\alpha)^{5/2}}. \qquad (50)$$

In practice, the expansion is far more accurate than that suggested by the order of the error, because the $\beta_{1j}$ values decrease rapidly with increasing j, when $\alpha_L$ and $\alpha_R$ are not substantially different from each other. A five to six digit accuracy is obtained from the expansion when compared to the numerical result. For computations, it is noted that for the first case ($\alpha_L\alpha_R < \pi^2/4$), the root is bracketed between $\sqrt{\alpha_L\alpha_R}$ and $\pi/2$. A better upper bound than $\pi/2$ is given by $\beta_{10}$.

In one aspect, for data analysis, there appears to be little use for the larger roots. Rather, the magnitude of these roots and the associated amplitudes are useful for assessing the dominance of the first eigenmode in the response. For $\sqrt{\alpha_L\alpha_R} \leq \pi/2$, it is easy to see that $n\pi < \beta_{n+1} < (2n+1)\pi/2$.

For core lengths and diameters of particular interest, in one embodiment, with $V_L$ and $V_R \approx 25$ cm$^3$ at a minimum, the third case ($\alpha_L\alpha_R > \pi^2/4$, but is less than $\pi^2$) does not occur in practice. Nevertheless, for completeness, it is noted that the first root is bounded by $\pi/2$ and $\sqrt{\alpha_L\alpha_R}$. The subsequent roots are such that $n\pi < \beta_{n+1} < (2n+1)\pi/2$.

For the fourth case ($\alpha_L\alpha_R > \pi^2/4$), the lower and upper bounds are again given by $\pi/2$ and $\pi$ for the first root. The subsequent root brackets depend on the value of $\alpha_L\alpha_R$. Let $(2n-1)\pi/2 < \sqrt{\alpha_L\alpha_R} < (2n+1)\pi/2$. The first n−1 roots are bracketed by $(2i-1)\pi/2$ and $i\pi$, with $i<n$. The subsequent root $\beta_n$ is bounded by $(2n-1)\pi/2$ and $\sqrt{\alpha_L\alpha_R}$ and the one following that has bounds $\sqrt{\alpha_L\alpha_R}$ and $(2n+1)\pi/2$. Past these roots, the brackets are $(2i-3)\pi/2$ and $(2i-1)\pi/2$, where $i > n+1$.

In one embodiment, an experiment involves measuring the decay in pressure difference between the upstream (left) side and the downstream (right) side of the sample. Therefore, $v(0,\tau)-v(1,\tau)=\delta v(\tau)$ is considered written according to (see equation (31))

$$\delta v(\tau) = \sum_1 A_n e^{-\beta_n^2\tau}\left[\frac{\alpha_L}{\beta_n}(\cos\beta_n - 1) - \sin\beta_n\right] \qquad (51)$$

In one embodiment, the results of the above sum are compared with the experimental data and the appropriately prescribed best match for permeability is obtained. According to another embodiment, a calculation based on $\beta_1$ is sufficient. Accordingly, $$\delta v(\tau) \approx A_1 e^{-\beta_1^2\tau}\left[\frac{\alpha_L}{\beta_1}(\cos\beta_1 - 1) - \sin\beta_1\right] \qquad (52)$$

even for short times, since $$A_1\left[\frac{\alpha_L}{\beta_1}(\cos\beta_1 - 1) - \sin\beta_1\right]$$

is close to $v_{L0}-v_{R0}$.

In one embodiment as described in more detail hereinafter, experimentally, starting with the sample and the upstream and downstream chambers at the same pressure, i.e., with valves 45R and 45L initially open, valve 45L is closed and the gas pressure in the upstream chamber 30 is increased by a small (perturbation) percentage (e.g., 10% or less). At time t=0, valve 45L is opened to permit equilibration and pressures $P_L(t)$ and $P_R(t)$ are monitored by the pressure sensors 47L and 47R as a function of time. The difference in the pressures measured by sensors 47L and 47R ($P_L(t)-P_R(t)$) is then characterized. If the decay is observed to be exponential, the characteristic decay time $T_d$ is obtained from $$P_L(t)-P_R(t) = (P_{L0}-P_{R0})\exp(-t/T_d). \qquad (53)$$

Converting equation (52) to a dimensional form results in the permeability k of a sample being calculated according to $$k = \frac{\phi\mu L^2 G_f}{T_d \beta_1^2 P_f} \qquad (54)$$

where $\phi$ is the porosity, $\mu$ is the shear or dynamic viscosity of the fluid (gas), L is the length of the sample, $G_f$ is obtained from equation (17), $P_f$ is the final pressure and $T_d$ is obtained from equation (53). Since the betas ($\beta$) depend only on $\alpha_L$ and $\alpha_R$, they are known either from equation (32) or the perturbation representation whose accuracy is known a priori. In one embodiment, $P_f$ is determined by fitting an exponential decay curve of the form $P_L(t)=P_{fL}+C_L\exp(-t/T_d)$ and $P_R(t)=P_{fR}+C_R\exp(-t/T_d)$ after ignoring the first few points, and then taking the mean of $P_{fL}$ and $P_{fR}$.

If a single exponential decay is not observed in experimental data from t=0, in one embodiment, the initial portion of the decay is ignored and $T_d$ is obtained from an arbitrary starting time from which an exponential relaxation is observed. In one embodiment, the initial one to two seconds of data is discarded. In one aspect, it is desirable to have negligible offset between the transducers on the left and the right side in the neighborhood of $P_f$ as established by the previously described calibration routine.

Figure 1B:
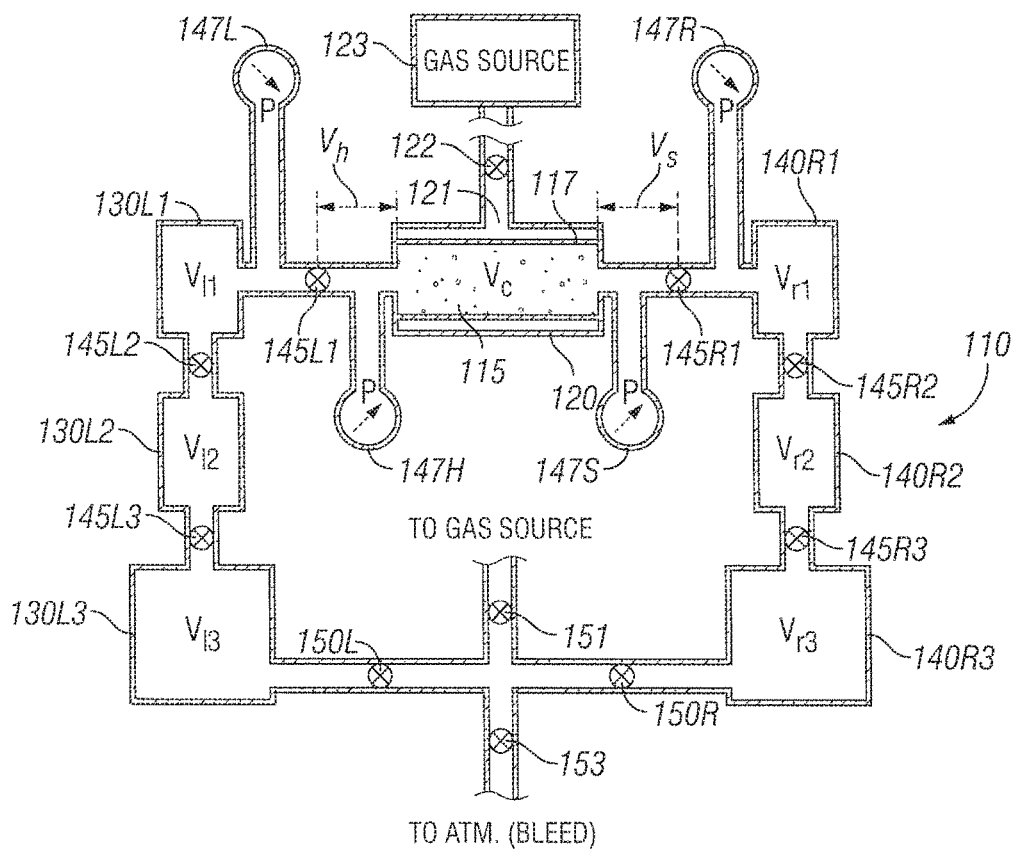
FIG. 1B is a schematic of another embodiment of an apparatus useful in measuring permeability and/or porosity of a solid sample.

Turning now to FIG. 1B, an embodiment of an apparatus 110 for measuring permeability and/or porosity of a sample 115 is seen. Sample 115 is shown tightly contained in a rubber jacket 117. Surrounding the rubber jacket is a metal cylindrical chamber 120. Chamber 120 has an inlet/outlet 121 with a valve/pressure regulator 122 that is coupled to a gas source 123. In this manner, a desired regulated confining or squeeze pressure(s) may be provided to the rubber jacket 117 and hence to the sample 115. To one side (e.g., "upstream") of the sample chamber 120 are located, in series, a sequence of chambers 130L1, 130L2, 130L3 with respective volumes $V_{l1}$, $V_{l2}$ and $V_{l3}$ and to the other side (e.g., "downstream") of the sample chamber 120 are located, in series, a similar sequence of chambers 140R1, 140R2, 140R3 with respective volumes $V_{r1}$, $V_{r2}$ and $V_{r3}$. Between the chambers on the left side are valves 145L1, 145L2, 145L3 respectively located between sample chamber 120 and chamber 130L1, chamber 130L1 and chamber 130L2, and chamber 130L2 and chamber 130L3. Pressure sensor 147L and optional pressure sensor 147H are located respectively between chamber 130L1 and valve 145L1, and between valve 145L1 and sample chamber 120. Similarly, between the chambers on the right side are valves 145R1, 145R2, 145R3 respectively located between sample chamber 120 and chamber 140R1, chamber 140R1 and chamber 140R2, and chamber 140R2 and chamber 140R3. Pressure sensor 147R and optional sensor 147S are located respectively between chamber 140R1 and valve 145R1, and between valve 145R1 and sample chamber 120. Feedback control regulators 150R and 150L are located between the gas source 123 and chambers 130L3 and 140R3 as well as an optional valve 151. A bleeder valve 153 to the atmosphere may also be provided.

In one embodiment, the pore volume $V_c$ of core 115 in sample chamber 120 is between 1 and 10 cc. In another embodiment, the core 115 in the sample chamber 120 has a volume $V_c$ of between 4 and 8 mL. In one embodiment, the jacket 117 in sample chamber is approximately 2.54 cm in diameter and 5.1 cm long, and the core sample is approximately 2.54 cm in diameter and between 1.25 cm and 5.1 cm long. The volume of $V_h$ which includes the coupling between valve 145L and sample chamber 120 and the coupling between pressure sensor 147H (if provided) to the coupling between valve 145L and the sample chamber 120 is chosen to be small and is typically similar in volume to the pore volume of the sample. For example, in one embodiment, volume $V_h$ is between 4 and 10 mL. The volume of $V_s$ is made as close to the volume of $V_h$ as possible. In one embodiment, the volume of chambers 130L1 and 140R1 are chosen to be significantly larger than the pore volume. For example, the volume of chambers 130L1 and 140R1 may be chosen to be between 15 and 30 mL, or more particularly 25 cc. In one embodiment, the volume of chambers 130L2 and 140R2 are chosen to be greater than the volume of the pore volume. For example, the volume of chambers 130L2 and 140R2 may be chosen to be about 15 mL. In one embodiment, the volume of chambers 130L3 and 140R3 are chosen to be significantly larger than the volume of the pore volume. For example, the volume of chambers 130L3 and 140R3 may be chosen to be about 30 mL. The volume of each chamber 130L 1-130L3 and 140R1-140R3 is effectively defined as the volume between valves upstream and downstream of that chamber. Thus, in the case of chamber 130L1, the volume includes the volume of the chamber itself as well as the couplings to valve 145L1 and valve 145L2, whereas in the case of chamber 140R2, the volume includes the volume of the chamber itself as well as the coupling to valve 145R2 and 145R3. In one embodiment, additional even larger chambers (e.g., 100 mL) are provided in series between the feedback control regulators 150L and 150R and chambers 130L3 and 140R3 respectively.

Through calibration, volumes for chambers 130L1, 130L1+130L2, 130L1+130L2+130L3, 140R1, 140R1+140R2 and 140R1+140R2+140R3 are known as described above with reference to equations (10A)-(10L). A choice is made at a beginning of an experiment as to whether the volumes in fluid connection to the sample in the sample chamber is to be relatively "tiny," "small," "medium" or "large." For tiny volumes, the upstream volume in fluid connection to the sample $V_L$ equals the volume $V_h$ (as further described below). For small volumes, the upstream volume in fluid connection to the sample $V_L$ equals the volume of chamber 130L1 plus $V_h$. For medium volumes, the upstream volume is the sum of the volumes of chambers 130L1 and 130L2 plus $V_h$. For large volumes, the upstream volume is the sum of the volume of chambers 130L1, 130L2, and 130L3 plus $V_h$. Corresponding definitions apply to the downstream volumes.

By way of example only, a medium volume is chosen as an option. The pressure transducers are precalibrated and only small drift and variability in the range of interest is adjusted by local shift calibration. Local shift calibration is done by closing valves 145L1 and 145R1 and opening the other valves. Approximately, the right side desired pressure $P_{r0}$ is set from the gas source and pressure readings $P_{r0}^{(l)}$ and $P_{r0}^{(r)}$ of the left and right transducers 147L and 147R. Next, the pressure is elevated and $P_{l0}$ and pressure readings $P_{l0}^{(l)}$ and $P_{l0}^{(r)}$ are noted. Given these values, equations (10N) and (10O) are sufficient to compute shift-calibrated $P_l$ and $P_r$.

The experiment (with the choice of medium volumes) has all valves open initially. The confining stress is chosen to be $P_{l0}$ (which is so for the first set of experiments in a newly loaded sample chamber). Valve 145L1 is in a closed state. Pressure is set to $P_{r0}$ by regulating gas from the source. Subsequently valve 145L1 is opened, dropping the left side pressure slightly below $P_{r0}$. Regulator valves 150L and 150R are then shut and equilibration of pressure between the left and right sides is monitored. Once they are within a certain tolerance, the confining pressure may be gradually increased to the desired value. Upon the left and right pressures agreeing within a tight tolerance, valve 145L1 is shut, and pressure on the left side is increased to $P_{l0}$. At this point valves 145L3 and 145R3 are shut. Since no resistance to flow is present on the left side with valve 145L3 shut, $P_{l0}$ is reached quickly.

At time zero, valve 145L1 is opened. Pressures on the shift-calibrated transducers are continuously monitored, and equations (10N) and (10O) are used to output $P_l$ and $P_r$ from the measured $P^{(l)}$ and $P^{(r)}$. The difference between $P_l$ and $P_r$ changes with time in accordance with the theoretical result of equation (51). Within a short time (e.g., a couple of seconds to a few minutes), the behavior predicted by equation (53) is obtained and the measurement may be used to infer $T_d$. Equation (54) is then used to get the first pass result for permeability.

The tiny option is chosen when the expected permeability is sub-microDarcy; i.e., in the range of tens to hundreds of nanoDarcies. Here the calibration of the two pressure transducers 147H and 147S in close proximity to the sample chamber is accomplished by leaving valves 145L1 and 145R1 open when setting the calibration pressures of $P_{r0}$ and $P_{l0}$. After the first equilibration of $P_{r0}$ with valve 145L1 being shut, the pressure is elevated to $P_{l0}$. Valve 145L1 is opened and then shut within a few seconds (e.g., 2-5 seconds). The transient $T_d$ is interpreted from the difference in pressures between the adjusted transducer pressures of sensors 147H and 147S.

In one embodiment, $V_h$ may be recomputed depending upon the length of the sample in the rubber jacket. In particular, assume that the calibrated volumes are known. For a given sample length L, this means that $V_h$ to the sample face is known. However, if the sample length is different than the standard metal cylinders (bored and solid) used to determine volumes an adjustment can be made. For small differences, the difference in volume due to the shorter (less volume) or longer (more volume) sample is added or subtracted to $V_h$ and $V_s$. Care is taken to properly center the sample. For larger differences, metal cylindrical shells are used as fillers on either side of the sample (in order to hold the rubber jacket open) and the volumes $V_h$ and $V_s$ are adjusted, taking care to account for the metallic volume of the shell.

Figure 2:
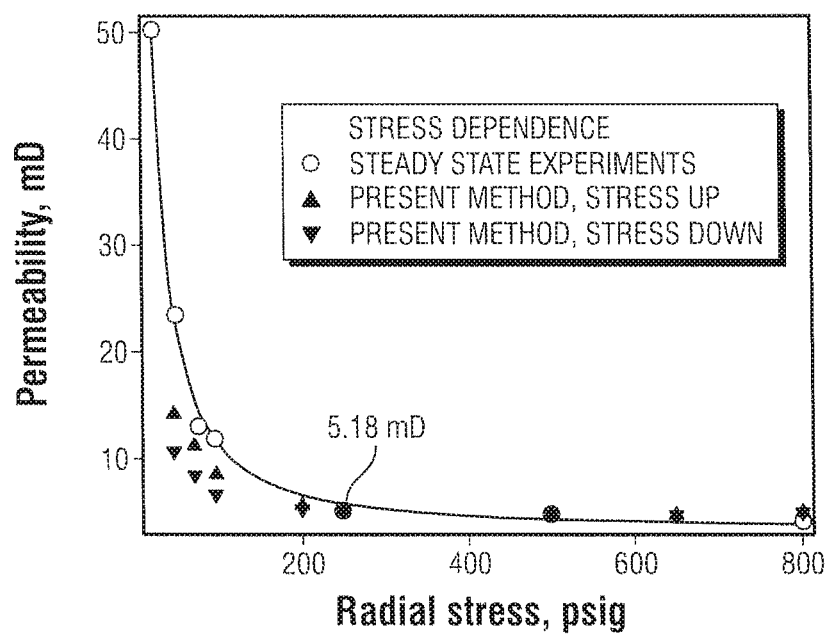
FIG. 2 is a plot of permeability as a function of radial stress comparing results of methods of the disclosure with a steady state experiment.

According to one embodiment, the apparatus and method previously described for measuring the permeability of a sample is found to be reliable for a wide range of permeabilities, from approximately 0.5 µD to about 100 mD. In particular, results obtained from an apparatus such as shown in FIG. 1B, and utilizing a method as previously described were compared to a steady-state measurement permeameter device described in U.S. Pat. No. 5,832,409 having a specified permeability measurement range of 0.1 mD to 20 D. A sample whose permeability at a confining radial stress of 250 psig was 5.18 mD (as measured by the steady-state permeameter) was tested in a series of experiments. Over the series of experiments, the sample contained in the sample cell was subjected to increasing radial stresses (e.g., 50 psig, 75 psig, 100 psig, 200 psig, 250 psig, 500 psig, 650 psig, 800 psig) and then decreasing radial stresses at the same radial stress levels. For each radial stress level, the experiment involved increasing the upstream pressure slightly above the sample and downstream pressure, monitoring the upstream and downstream pressures over time, characterizing the decay according to equation (53), and finding the permeability according to equation (54). A plot of the resulting determinations of permeability as a function of the radial stress is shown in FIG. 2 where the steady-state determinations are shown. It is noted that while the results are in good agreement for radial stresses of 250 psig and above, under approximately 200 psig, the permeability determined according to the present method does not agree particularly well with the steady-state experiments. This is believed due to the variability of the rubber hardness at lower radial stresses of the rubber boots utilized to isolate the sample in its chamber.

Figure 3:
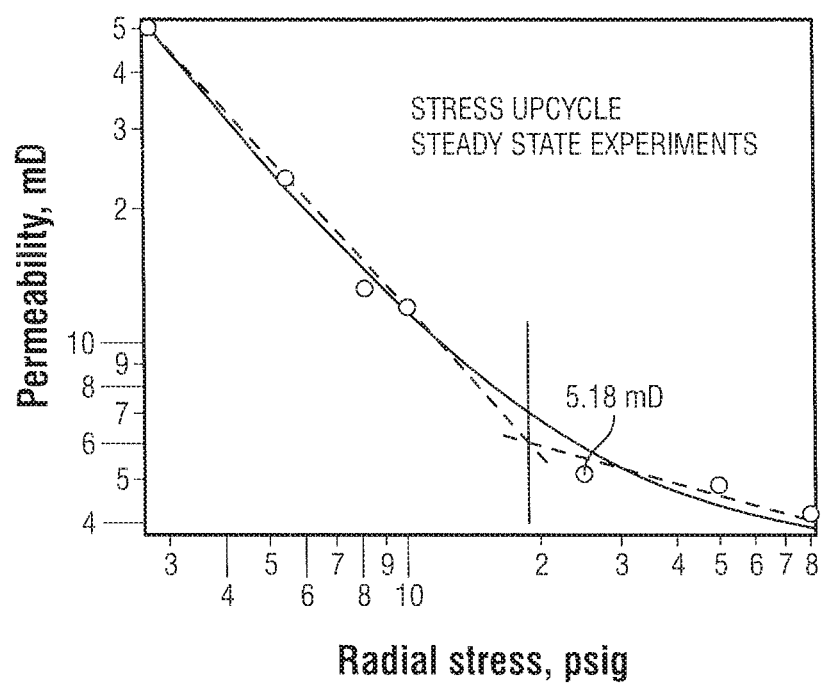
FIG. 3 is a plot of permeability as a function of radial stress for steady state experiments.

FIG. 3 plots steady-state gas permeability measurements assuming ideal gas for the sample (as in Equation (3)) and reveals two distinct power law behaviors (dotted lines). In particular, a qualitatively different behavior above about a 200 psig radial stress is evident from FIG. 3. It is therefore quite possible that in this embodiment, 200 psig or thereabouts is the minimum stress required for the lateral surface seal of the steady-state permeameter apparatus to take effect.

Figure 4:
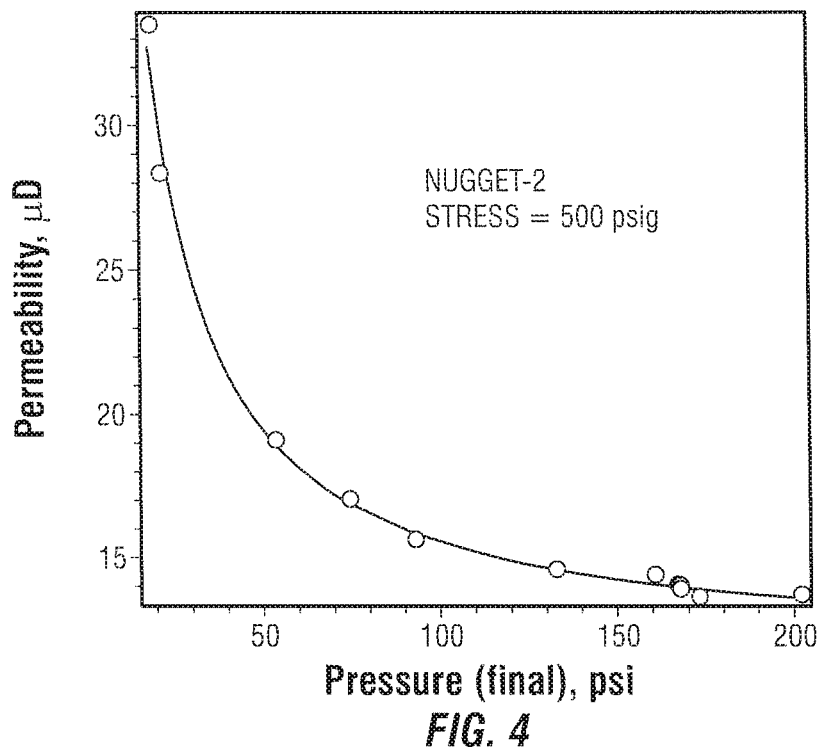
FIG. 4 is a plot of permeability as a function of final pressure.

In one aspect, for sufficiently low permeability of a few mD and below, a significant gas pressure effect induced by slip at the pore walls is evident. FIG. 4 plots the determined permeability of an ultra-low permeable sandstone core sample having a length of 1.25 cm that was placed under a radial stress of 500 psi in an apparatus such as shown in FIG. 1A or FIG. 1B. In FIG. 4, data is provided for a sample of about 15 µD as a function of final pressure $P_f$. The fitted curve to the data points is a Klinkenberg correction to permeability of the form $$k = \left(k_0 + \frac{k_1}{P}\right) \quad (55)$$

where $k_0$ is the permeability of a liquid or very high pressure gas, $k_1$ is a constant and P is the pressure. Experiments were restricted to a gas pressure of 200 psi in order to limit the stress related alteration of permeability. Note the expanded y-axis, demonstrating the sensitivity of the apparatus.

Figure 5:
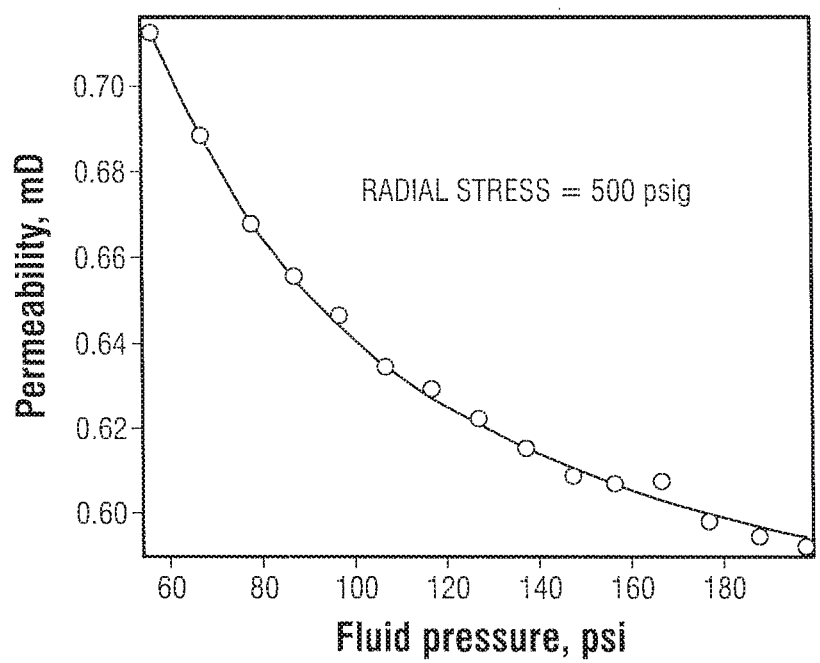
FIG. 5 is a plot of permeability as a function of fluid (gas) pressure.

A second sample with a permeability of about 0.6 mD was used extensively to study the validity of the interpretation and variability with respect to gas pressure. This sample was sufficiently consolidated and showed only small variations in permeability with respect to stress. The inferred permeability at a radial stress of 500 psi at different gas pressures $(P_f)$ with a pressure differential $P_{l0}-P_{r0}$ of 10 psi (except at the low pressure end, where a smaller difference of 4 psi was used) is shown in FIG. 5 where results of experiments covering a range of approximately 60 psi to 200 psi are shown. A measurable slip correction leading to increased observed permeability is evident from these results. The changes are small but measurable by the devices of FIGS. 1A and 1B. At the nominal pressure of 190 psi, the decay time constant was 41.83 seconds, whereas at the lowest pressure of about 60 psi, the decay time constant was 120.26 seconds. The final permeability differs by only about 20%. The method is seen to be robust, and the correction due to variation of gas compressibility with respect to pressure is the most important. The Klinkenberg curve is also shown in FIG. 5. No additional correction due to effective stress variation was necessary because the sample does not show appreciable variation due to stress at a fixed gas pressure.

In one aspect, the procedure to obtain permeability is as follows. After solenoid operation, a few data points are discarded and then the difference between $P_L(t)$ and $P_R(t)$ (see equation (53)) is processed in order to infer the decay time constant $T_d$ and therefore the permeability k according to equation (54). No other quantity is adjustable.

Once permeability is determined, it is possible to predict $P_L(t)$ and $P_R(t)$ (the pressures upstream and downstream of the sample over time) from first principles and the known values of the porosity $\phi$, and the pressures at the beginning of the experiment of the adjacent chambers, $P_{l0}$ and $P_{r0}$. An independent confirmation of the operational technique is thus possible. Of course, in view of the short-time scale of the experiments, the finite time required for the solenoid operation, and the signal processing induced time-delay of the pressure measurement a perfect match is not expected. However, a close match would be good confirmation.

Figure 6:
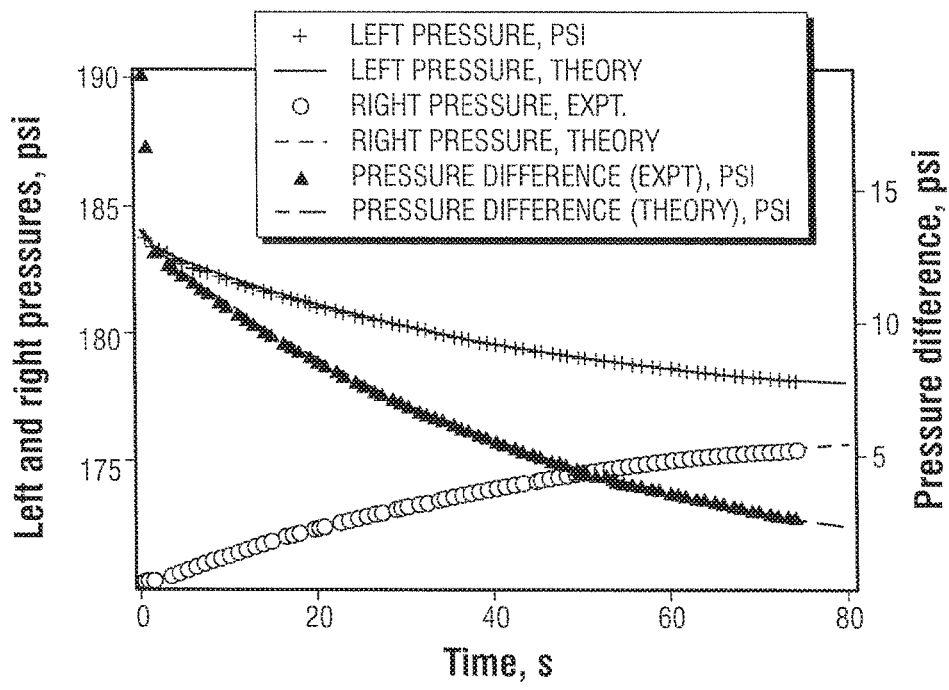
FIG. 6 is a plot of left and right pressures and their difference as a function of time.
Figure 7:
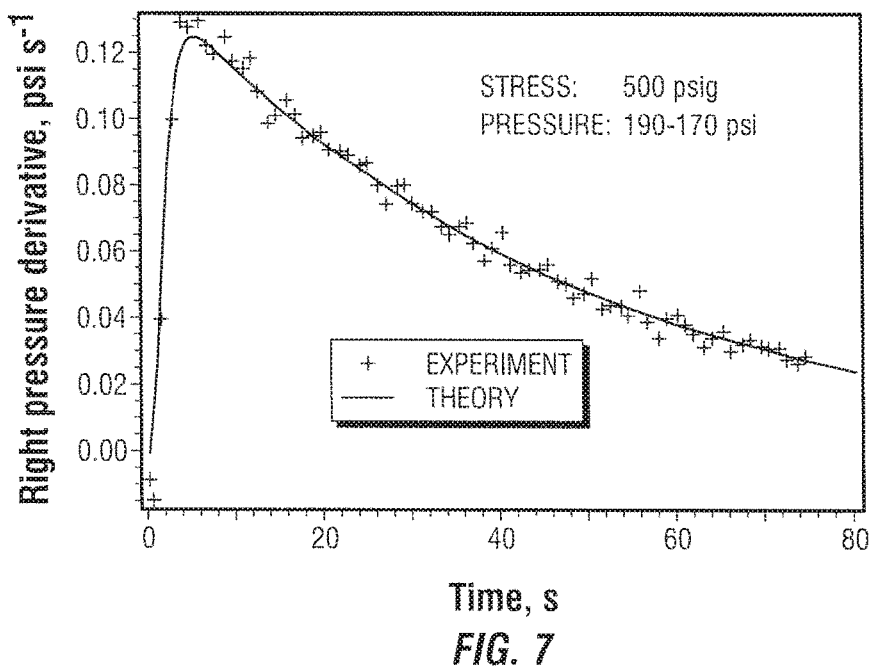
FIG. 7 is a plot of right pressure derivative as a function of time.

In FIG. 6 the theoretical and experimental curves obtained are shown when the initial left and right side pressures were 190 psi and 170 psi respectively. The abrupt drop close to t=0 is due to the opening of left solenoid. An excellent match is obtained for the right side pressure, including the delay in the pressure rise. There is a very small timing/absolute pressure mismatch in the left side, quite negligible on the scale shown. Otherwise the match is excellent. A more noteworthy comparison is between the measured and the theoretical time derivative of pressure of the right side. The excellent match between the two is illustrated in FIG. 7 which shows a pressure transient during an equilibration where the initial pressure differential was about 20 psi. In dimensionless form, the pressure in the right hand side is $$v(1,\tau) = \sum_l A_n e^{-\beta_n^2 \tau}\left[\sin\beta_n - \frac{\alpha_L}{\beta_n}\cos\beta_n\right] \quad (56)$$

so that the peak rate of change occurs at a dimensionless time $\tau_M$ obtained by solving $$\sum_1 -\beta_n^4 A_n e^{-\beta_n^2 \tau_M} \left[\sin\beta_n - \frac{\alpha_L}{\beta_n}\cos\beta_n\right] = 0. \quad (57)$$

In one aspect, permeability may be inferred rapidly utilizing dimensionless time $\tau_M$ because as shown in FIG. 7, the peak is reached in a matter of seconds (e.g., about 5.5 seconds in FIG. 7). Permeability is inferred as follows. First, a theoretical value of a dimensionless peak value time $\tau_M$ is assumed. Then, the peak value time $t_M$ determined according to the experiment is compared to the theoretical value with the ratio of the two ($t_M/\tau_M$) being equal to the time scale $T_T$ which is a function of the permeability k of the equilibration pressure. More particularly, as set forth in equation (23), $$T_T = \frac{\phi L^2 G_f}{\lambda_f P_f}$$

where $\lambda_f = k/\mu$. It is noted that since equation (23) requires knowledge of $P_f$, that it may take more time to find $P_f$ than to find the peak time $t_M$. However, as set forth below with respect to FIG. 8, $P_f$ may be quickly found as the average of the upstream and downstream pressures when the left and the right volumes are nearly equal and are much larger than the core volume. Otherwise equation (62) below may be utilized or the embodiment described hereinafter with respect to FIG. 12 may be utilized to infer $P_f$. Thus, in a very short time, low permeabilities may be inferred.

Figure 8:
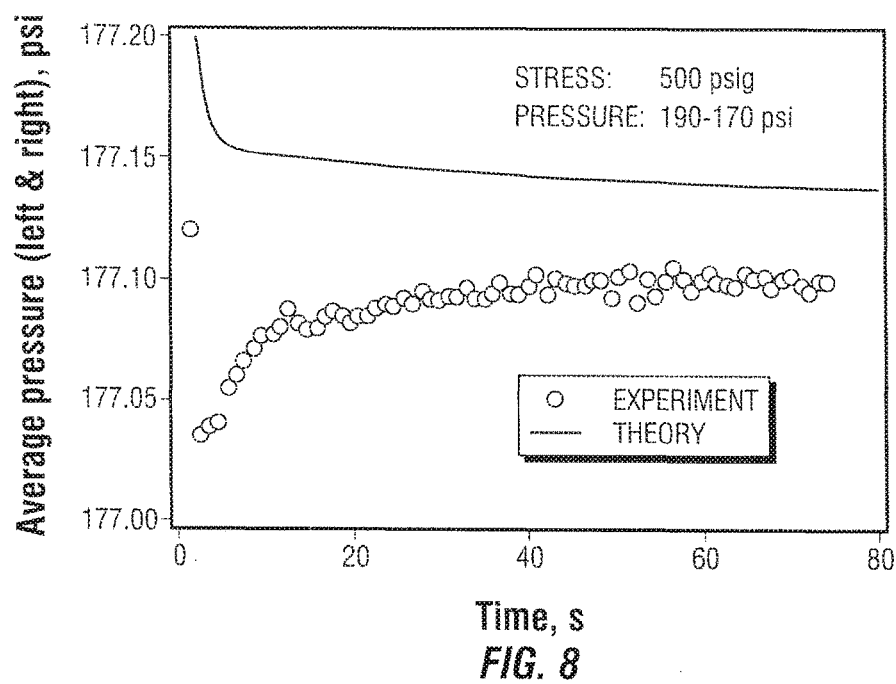
FIG. 8 is a plot of average pressure as a function of time.

In FIG. 8, the average pressure $$\frac{1}{2}(P_L(t) + P_R(t))$$

measured by the pressure sensors of the apparatus is compared with the theoretical results of an experiment with the radial (squeezing) stress on the sample set at 500 psig, an initial upstream pressure of 190 psi and an initial downstream pressure of 170 psi. Although the absolute difference is quite negligible, and tends to zero (on an average over several runs) for t→∞, the trend to zero is opposite to that of theory. The experimental extrapolated pressure averaged over several runs matches that of theory within the resolution of the transducers. The theoretical final pressure estimate is known at the start of the experiment and is sufficient to use in equation (23) for samples whose porosity is known.

Interpretation based on $dP_R/dt$ is evident now. It is unaffected by adiabatic expansion. In some cases, the time resolution may limit this to very small permeabilities. This is precisely where such a measurement is desirable, because minor temperature changes, transducer drift, and leaks, while irrelevant on a time scale of hundred seconds, can impact the measurement over an hour.

Figure 9:
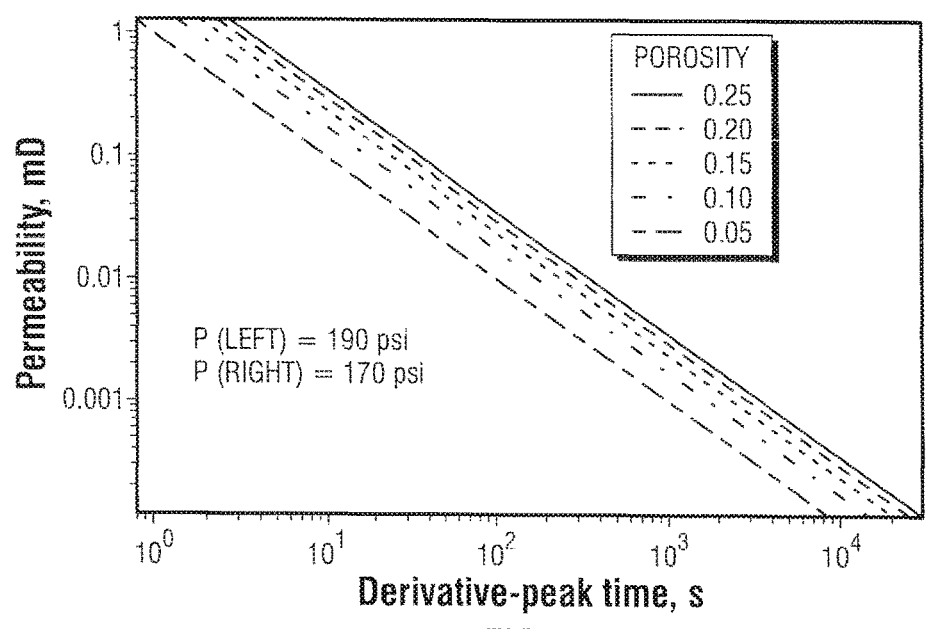
FIG. 9 is a plot of permeability as a function of derivative-peak time.

Since the porosity may be known before the start of the experiment, a useful correlation is obtained by fixing $P_{l0}$ and $P_{r0}$, and computing permeability as a function of the observed time for the peak in $dP_R/dt$ (i.e., the time derivative of the downstream pressure signal) such as shown in FIG. 7. This cross-plot which is shown in FIG. 9 for five different porosities, is useful for inferring permeability. For example, using the cross-plot of FIG. 9 that was generated for a sample having a length L=5.08 cm, a diameter D=2.54 cm, where $V_f = V_r = 25$ ml (at 21° C.), for a sample having a porosity of 0.25, if the derivative peak time is 10 seconds, the permeability is determined to be approximately 0.4 mD. As another example, using the cross-plot of FIG. 9, for a sample having a porosity of 0.05, if the deriative peak time is 60 seconds, the permeability is approximately 0.02 mD (20 μD).

In one aspect, while the peak derivative method is useful for verifying the permeability calculated from the exponential decay, the method may be affected by the time scales dictated for initial equilibration. A larger tolerance during equilibration and $P_{l0}-P_{r0}$ provides permeabilities within acceptable errors.

Given that the rock petrophysical properties show hysteretic stress dependence, the precise sequence for characterization is not easily determined, since the Biot coefficient $\alpha_B$ is also unknown. Furthermore, upon lowering of $P_f$ while the effective stress increases causing a permeability reduction, slip causes an increase in the measured permeability. In one embodiment, a power law reduction in permeability of the form $$k = k_0(\sigma - \alpha_B P)^{-\psi} \quad (58)$$

is found for sufficiently large stresses and fluid (gas) pressure. Generally, it might be expected that $k_0$, $k_1$, $\alpha_B$ and $\psi$ will vary with the stress cycle history.

In one embodiment, the measurement method for permeability may also be used to infer porosity. However, for an explicit permeability computation, porosity should be inferred first. Therefore, in one embodiment, porosity is first computed as discussed below, and then permeability is inferred.

Assume that the zero and the range offset corrections for the transducers have been carried out as previously described. From mass balance, $$V_L \rho_{L0} + V_R \rho_{R0} + V_c \rho_{R0} = V_f \rho_f \quad (59)$$

where $V_f = V_L + V_R + V_c$. Dividing the mass balance equation by $V_c$, and solving for $P_f$, the following is obtained:

$$P_f = \alpha\left(P_{LO}\frac{z_f}{\alpha_L z_{LO}} + P_{RO}\frac{z_f}{\alpha_R z_{RO}} + P_{RO}\frac{z_f}{z_{RO}}\right) \quad (60)$$

where $\alpha = \dfrac{1}{\dfrac{1}{\alpha_L} + \dfrac{1}{\alpha_R} + 1}$.

Conversely, if $P_f$ is known, equation (59) may be used to solve for $V_c$, i.e., $$V_c = V_L \frac{\rho_f - \rho_{LO}}{\rho_{RO} - \rho_f} - V_R \quad (61)$$

from which the porosity $\phi$ can be calculated in that the porosity is the pore volume $V_c$ divided by the total volume of the sample. In one embodiment this requires that $V_R$ and $V_L$ be comparable to $V_c$ and requires very accurate pressure measurements.

In one aspect, a more difficult issue is the diffusion into the core as pressure equilibration through expansion from volume $V_l$ to $V_h$ takes place. It is for this reason that in one embodiment, the initial pressure $P_{l0}$ is used to infer porosity rather than $P_{L0}$. Using equation (8) for $\rho_{L0}$ in equation (61), the core volume in terms of $P_{l0}$ and $P_{R0}$ is $$V_c = V_L \frac{\left(\frac{P_f}{Z_f} - \frac{V_l}{V_L}\frac{P_{lO}}{Z_{lO}} - \frac{V_h}{V_L}\frac{P_{RO}}{Z_{RO}}\right)}{\frac{P_{RO}}{Z_{RO}} - \frac{P_f}{Z_f}} - V_R. \quad (62)$$

As will be appreciated, equation (62) does not depend upon knowing the pressure $P_{LO}$ that is reached instantly after valve 45L is opened. Thus, by running an experiment with known volumes and controlled initial pressures, and finding an equilibration pressure or expected equilibration pressure $P_f$, the core pore volume $V_c$ is found. Conversely, if $V_c$ is known, $P_f$ may be inferred. Dividing the core pore volume by the total core volume yields the porosity; i.e., $\phi = 4V_c/(\pi L D^2)$.

In one embodiment, in order to measure permeability rapidly and accurately, $\alpha_L$ and $\alpha_R$ should be $\ll 1$. Since $V_c$ is then small compared to $V_L$ and $V_R$, and the pore volume $V_c$ in equation (62) is obtained by subtraction of quantities much larger than $V_c$, errors can propagate disproportionately. In one embodiment, temperature changes during the course of the experiment and small errors in the transducer need to be avoided. It is for this reason that very accurate relative pressure calibration can be desirable. As previously discussed, post absolute pressure calibration, each experiment can be preceded by an automated relative transducer adjustment. In one embodiment, forced ventilation is used to counteract heat dissipation from the solenoids and to thereby maintain temperature in the apparatus.

For interpretation of permeability, in one embodiment, an independently measured porosity is used, the final pressure is calculated from equation (60), and the final pressure is compared to the projected $P_f$ obtained from experimental data (see, FIG. 6 and equations). Agreement between the two verifies consistency. A significant departure usually indicates leaks from or into the system. In the previously described apparatus, an excellent comparison between the theory and the experiment for the final pressure has been obtained across a range of pressures and stress, usually agreeing to within 200 Pa on a pressure difference scale of about 70000 Pa, an accuracy better than 0.3 percent.

The sensitivity to porosity may be increased by elevating $P_{lO} - P_{rO}$. A late time transient still provides permeability at $P_f$.

A table of porosities for one sample is given along with the left and right side gas pressures in Table 1. Table 1 was generated using experimental data. While there are fluctuations from one experiment to another, the mean value is in excellent agreement with the pycnometer data.

TABLE 1

Pressure and porosity values; $\Delta P_f$ is the experimental minus the theoretical estimate. Porosity from pycnonmetry was 0.1714.

| $P_{lO}$ | $P_{rO}$ | $\phi$ | $\Delta P_f$ |
|---|---|---|---|
| 203.759 | 191.434 | 0.1228 | 0.103 |
| 203.180 | 190.282 | 0.1514 | 0.043 |
| 203.547 | 190.973 | 0.1561 | 0.032 |
| 193.437 | 181.397 | 0.1605 | 0.022 |
| 183.435 | 170.806 | 0.1731 | −0.004 |
| 173.183 | 159.965 | 0.1655 | 0.013 |
| 163.199 | 149.598 | 0.1740 | −0.006 |
| 153.518 | 140.848 | 0.2252 | −0.112 |
| 143.340 | 130.261 | 0.2082 | −0.080 |
| 133.394 | 119.979 | 0.1745 | −0.007 |
| 123.428 | 110.175 | 0.1757 | −0.010 |
| 113.597 | 100.399 | 0.1987 | −0.060 |
| 103.347 | 89.709 | 0.1604 | 0.025 |
| 93.582 | 80.074 | 0.1745 | −0.007 |
| 84.007 | 71.025 | 0.2028 | −0.067 |
| 73.628 | 59.667 | 0.1750 | −0.008 |
| 63.584 | 49.372 | 0.1843 | −0.030 |

Average $\phi = 0.1754$

In one aspect, using the methods and apparatus previously described, samples having permeability as low as 100 nD to about 50 mD have been successfully tested and measured. In another aspect, it is expected that using the methods and apparatus previously described, samples with lower and higher permeabilities may also be successfully tested and measured. In another aspect, a high degree of accuracy in pressure measurements enable porosity measurements for $\phi \geq 0.10$.

In one aspect, the gas pressure and the characteristics of stress should be specified adequately when permeability is assigned.

Various embodiments of the present disclosure can determine permeability and porosity while also accounting for adsorption of gases within the sample. The adsorption of the sample is accounted for by using an adsoprtion isotherm of the sample and gas. For a particular gas, the adsorption isotherm can be determined by performing experiments on the sample as is known in the art. For example, the adsorption isotherm can be determined by measuring changes in pressure of a gas that is introduced into a sample having a known porosity and pore volume. Initially, the gas is confined within a chamber at an initial known pressure. A valve separates the chamber from the sample. The sample is maintained at a pressure that is different from the initial known pressure. The valve is opened and the gas is introduced into the sample. The pressure of the gas in the chamber is measured again to determine a final pressure once the gas has had time to adsorb within the sample. The initial known pressure and the final measured pressure can be used to determine the adsoption isotherm for the gas within the sample. The above procedure can be repeated at different initial pressures to determine the adsoprtion isotherm. See, e.g., Nicholas P. Stadie, Synthesis and Thermodynamic Studies of Physisorptive Energy Storage Materials, California Institute of Technology (2013). In one aspect, the effects of adsorption can be included in the intepretation for permeability and porosity.

More particularly, tight gas sands may contain clays and organic matter that adsorb gases to varying extents. For sufficiently small pore dimensions, adsorption may reduce the effective pore radius. Since the extent of adsorption is expected to increase with gas-phase activity, permeability will vary not only with gas type but also gas pressure.

Any change in pressure may also affect porosity at a fixed stress of $\sigma$. At $P_f$, if it is appreciated that $$\frac{\partial \phi}{\partial P} P_f = c_{\phi f} P_f \ll 1,$$

then variations in porosity are higher order than $v$, and for simplicity such terms will be regarded as $o(v)$, since $$\phi = \phi_f + c_{\phi f} P_f v, \quad (63)$$

where $\phi_f$ is the porosity at $P_f$. In reality Darcy velocity is with respect to the solid. With bulk compressibility being $c_b$, the velocity of the solid is at most of order $c_b P_f$ in relation to gas. Since $c_b P_f \ll 1$, the solid velocity term is of higher order than $v$ and will not be considered. Using equation of state, the perturbed pressure for $v$, and porosity variation, in the absence of adsorption, the continuity equation $$\frac{\partial \phi \rho}{\partial t} + \frac{\partial \rho v_x}{\partial x} = 0 \tag{64}$$

may be simplified to $$\frac{M}{RT}\left[E_f G_f \phi_f \frac{\partial v}{\partial t} + E_f(1+vG_f)c_{\phi f} P_f \frac{\partial v}{\partial t} + c_{\phi f} P_f v E_f G_f \frac{\partial v}{\partial t}\right] + \frac{\partial \rho v_s}{\partial x} = 0. \tag{65}$$

where $E_f$ is a ratio of gas pressure to compressibility factor at pressure $P_f$ (as set forth in equation (17)), M is the molecular weight of the gas, R is gas constant, T is temperature. From the foregoing, it is evident that the second and third terms may be regarded as $o(v)$, resulting in $$\frac{M}{RT}\left[E_f G_f \phi_f \frac{\partial v}{\partial t}\right] + \frac{\partial \rho v_x}{\partial x} + o(v) = 0. \tag{66}$$

Accounting for adsorption alters the continuity equation. For an arbitrary adsorption isotherm, quasi-linearizing about the final pressure $P_f$, the adsorbed mass per unit pore volume may be written to be $$\eta = \eta_f + c_\eta P_f v \tag{67}$$

where, as before, the subscript f implies the value at $P_f$ and $c_\eta$ is the quasilinear adsorption coefficient at $P_f$. Including adsorption, the continuity equation becomes $$\frac{\partial \phi(\rho+\eta)}{\partial t} + \frac{\partial \rho v_x}{\partial x} = 0 \tag{68}$$

where the adsorbed gas has a zero velocity. It has already been shown that $$\frac{\partial \phi \rho}{\partial t} = \frac{M}{RT}\phi_f E_f G_f \frac{\partial v}{\partial t} + o(v). \tag{69}$$

The second time derivative term is $$\frac{\partial \phi \eta}{\partial t} = \phi_f c_\eta P_f \frac{\partial v}{\partial t} + \eta_f \frac{\partial \phi}{\partial t} + o(v). \tag{70}$$

Since by the previous discussion, the second term on the right is $o(v)$, the continuity equation along with Darcy's law results in $$\frac{M}{RT}\phi_f E_f G_f \frac{\partial v}{\partial t} + \phi_f c_\eta P_f \frac{\partial v}{\partial t} - \frac{M}{RT}\frac{P}{Z(P)}\lambda_f P_f \frac{\partial^2 v}{\partial x^2} = o(v), \tag{71}$$

which in dimensionless time and distance form simplifies to $$\left(1 + \frac{c_\eta P_f RT}{E_f G_f M}\right)\frac{\partial v}{\partial \tau} = \frac{\partial^2 v}{\partial \xi^2} + o(v). \tag{72}$$

Since the areal and lineal dimension variations due to changes in pressure do not contribute to the leading order, the boundary conditions remain the same as before.

To account for adsorption, it is useful to transform the time coordinate to $$\tau_\eta = \frac{\tau}{\left(1 + \frac{c_\eta P_{fRT}}{E_f G_f M}\right)}. \tag{73}$$

Then the governing equations are $$\frac{\partial v}{\partial \tau_\eta} + \frac{\partial^2 v}{\partial \xi^2} + o(v), \tag{74}$$

with the boundary conditions being $$\frac{dv_L(\tau)}{d\tau_\eta} = \alpha_{L\eta} \frac{\partial v(0,\tau)}{\partial \xi} + \ldots, \tag{75}$$

and $$\frac{dv_R(\tau)}{d\tau_\eta} = \alpha_{R\eta} \frac{\partial v(0,\tau)}{\partial \xi} + \ldots, \tag{76}$$

where $$\alpha_{L\eta} = \alpha_L\left(1 + \frac{c_\eta P_f}{E_f G_f}\frac{RT}{M}\right), \tag{77}$$

and $$\alpha_{R\eta} = \alpha_R\left(1 + \frac{c_\eta P_f}{E_f G_f}\frac{RT}{M}\right). \tag{78}$$

Thus, if the adsorption isotherm is known, the previous solution is readily used with $\alpha_{L\eta}$ replacing $\alpha_L$, and $\alpha_{R\eta}$ replacing $\alpha_R$, and with $\tau_\eta$ replacing $\tau$ for the dimensionless time. The interpretation proceeds as before, except that the adsorption isotherm is used to infer the quasilinear isotherm coefficient $c_\eta$ as a function of $P_f$.

As a consequence of a pressure decay experiment, knowing the characteristic decay time constant $T_d$, the permeability may be inferred from $$k = \frac{\mu \phi L^2 G_f}{\beta_{1\eta}^2 P_f T_d}\left(1 + \frac{c_\eta P_f}{E_f G_f}\frac{RT}{M}\right), \tag{79}$$

where $\beta_{1\eta}$ is calculated with $\alpha_{L\eta}$ and $\alpha_{R\eta}$ in lieu of $\alpha_L$ and $\alpha_R$.

In the absence of adsorption, the equation for porosity is the ratio of $V_c$ to AL. With adsorption, the mass conservation of gas is modified to $$V_L \rho_{L0} + V_R \rho_{R0} + V_c \rho_{R0} + V_c \eta_{R0} = V_f \rho_f + V_c \eta_f, \tag{80}$$

and the quasi-linearized adsorption equation $$\eta_{R0} = \eta_f + c_\eta P_f v_{R0}. \tag{81}$$

These equations may be solved to obtain the core pore volume as $$V_c = V_L \frac{\left(\frac{P_f}{Z_f} - \frac{V_l P_{l0}}{V_L Z_{l0}} - \frac{V_h P_{R0}}{V_L Z_{R0}}\right)}{\left(\frac{P_{R0}}{Z_{R0}} - \frac{P_f}{Z_f} + \frac{RT}{M}c_\eta(P_{R0} - P_f)\right)} - \tag{82}$$

$$V_R \frac{\left(\frac{P_{R0}}{Z_{R0}} - \frac{P_f}{Z_f}\right)}{\left(\frac{P_{R0}}{Z_{R0}} - \frac{P_f}{Z_f} + \frac{RT}{M}c_\eta(P_{R0} - P_f)\right)}.$$

Figure 10:
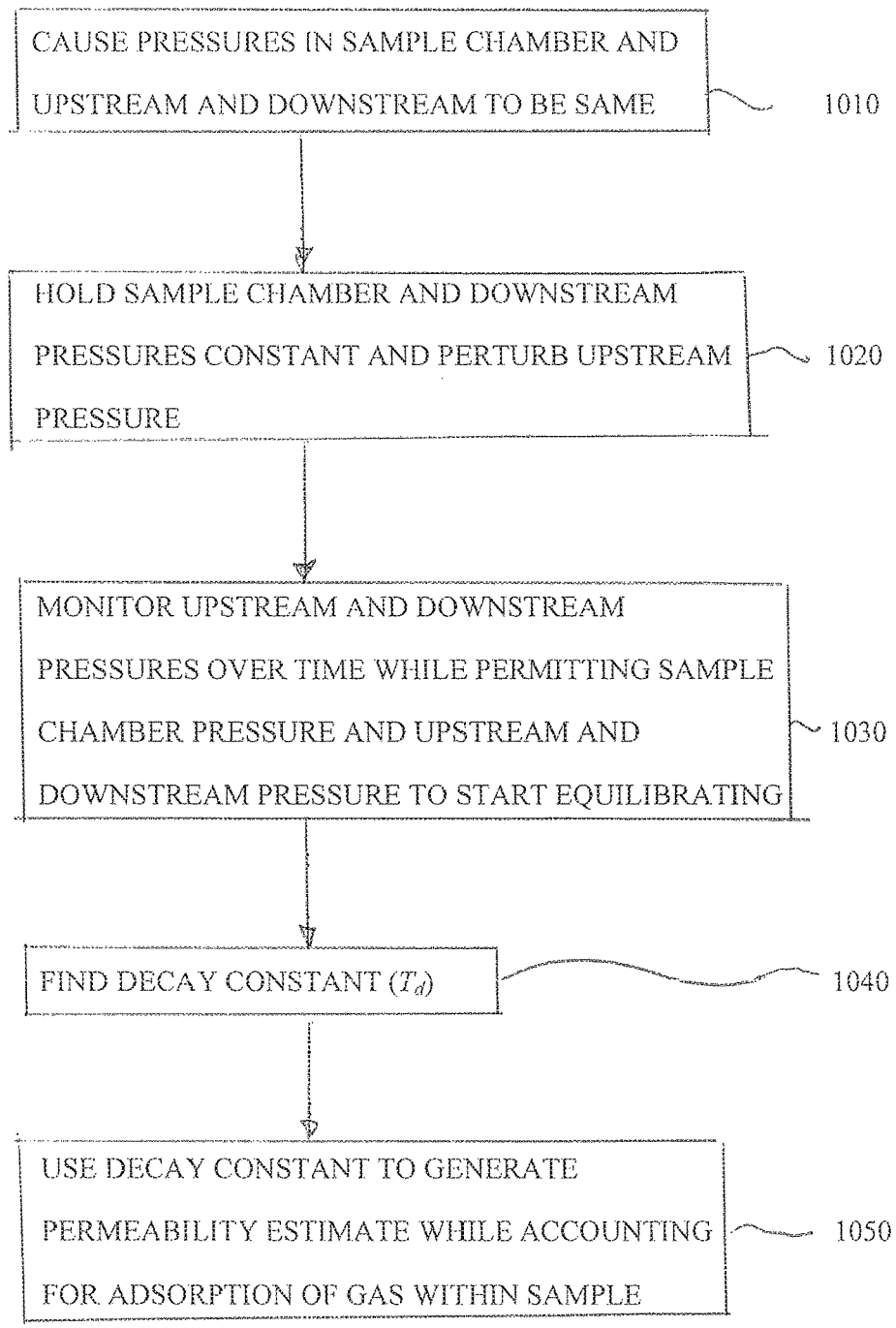
FIG. 10 is a flow diagram of one method of determining the permeability of an ultra-low permeable sample while accounting for adsorption.

Given the above, according to one embodiment, the permeability of an ultra-low permeability sample contained in a sample chamber can be determined while accounting for adsorption. Referring to FIG. 10, at 1010, and using a sample chamber as described above with reference to FIG. 1A or 1B, the pressures in the sample chamber and upstream and downstream of the sample chamber are caused to be the same. At 1020, the upstream pressure is changed by a perturbation percentage while holding the sample chamber and downstream pressures constant. At 1030, the upstream and downstream pressures are monitored as a function of time while permitting the sample chamber pressure and the upstream and downstream pressures to start equilibrating. At 1040, a decay constant ($T_d$) is found, e.g., according to equation (53), relating to the difference in the measured upstream and downstream pressures over time. At 1050, the decay constant is used, e.g., according to equation (79), to generate a permeability estimate of the sample while accounting for adsorption of gas within the sample. It will be appreciated that in finding the permeability according to equation (79), the quasilinear coefficient $c_\eta$ is utilized. The quasilinear coefficient for the isotherm at pressure $P_f$ may be known, or may have previously been determined by bringing gas into contact with the sample and measuring the adsorption isotherm as a function of pressure. It will also be appreciated that in finding the permeability according to equation (79), $\beta_{1\eta}$ is calculated according to equation (32) albeit utilizing $\alpha_{L\eta}$ and $\alpha_{R\eta}$ as set forth in equations (77) and (78) in lieu of $\alpha_L$ and $\alpha_R$. In particular $$\frac{\beta_{1\eta}(\alpha_{L\eta} + \alpha_{R\eta})}{\beta_{1\eta}^2 - \alpha_{L\eta}\alpha_{R\eta}} = \tan\beta_{1\eta}.$$

Figure 11:
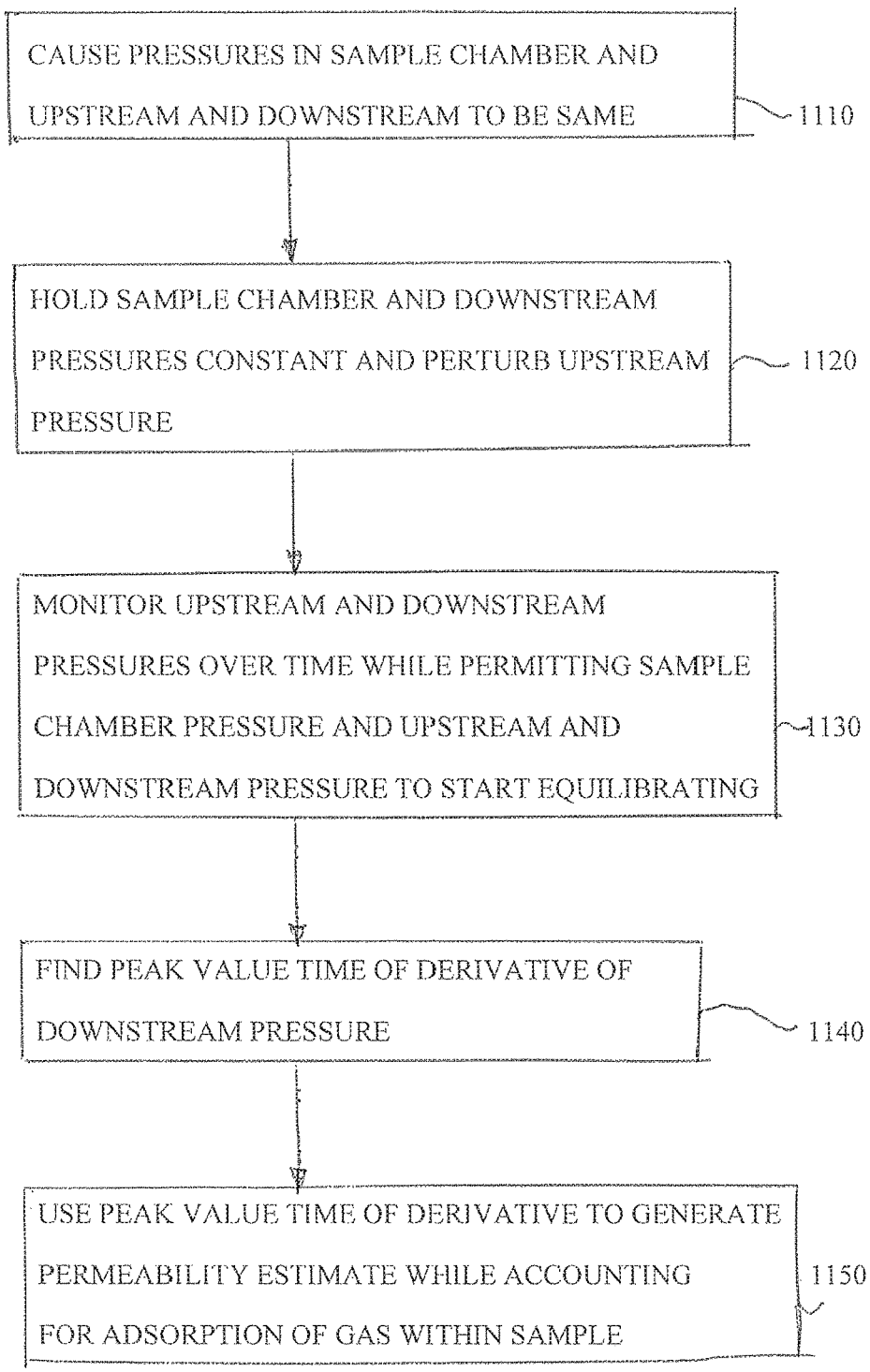
FIG. 11 is a flow diagram of another method of determining the permeability of an ultra-low permeable sample while accounting for adsorption.

According to another embodiment, the permeability of an ultra-low permeability sample contained in a sample chamber can be determined while accounting for adsorption utilizing a peak value time of a derivative of the downstream pressure signal. As seen in FIG. 11, at 1110 using a sample chamber as described above with reference to FIG. 1A or 1B, the pressures in the sample chamber and upstream and downstream of the sample chamber are caused to be the same. At 1120, the upstream pressure is changed by a perturbation percentage while holding the sample chamber and downstream pressures constant. At 1130, the upstream and downstream pressures are monitored as a function of time while permitting the sample chamber pressure and the upstream and downstream pressures to start equilibrating. At 1140, a peak value time of a derivative of the downstream pressure signal is found, and at 1150, the peak value time of the derivative is used, e.g., according $$T_T = \frac{\phi L^2 G_f}{\lambda_f P_f}$$

(as set forth in equation (23), where $\lambda_f = k/\mu$) to find the permeability estimate of the sample while accounting for adsorption of gas within the sample. It will be appreciated that in finding the permeability estimate, the time scale $T_T$ is determined. To find $T_T$ while accounting for adsorption, equation (32) is modified according to $$\frac{\beta_{n\eta}(\alpha_{L\eta} + \alpha_{R\eta})}{\beta_{n\eta}^2 - \alpha_{L\eta}\alpha_{R\eta}} = \tan\beta_{n\eta},$$

with $\alpha_{L\eta}$ as defined in equation (77) and $\alpha_{R\eta}$ as set forth in equation (78). Also, equation (42) is modified with $A_n$ being replaced by $A_{n\eta}$ according to $$A_{n\eta} = \frac{v_{R0}\int_0^1 H_n(\xi)d\xi + \frac{v_{L0}}{\alpha_{L\eta}}H_n(0) + \frac{v_{R0}}{\alpha_{R\eta}}H_n(1)}{\int_0^1 H_n^2 d\xi + \frac{H_n^2(0)}{\alpha_{L\eta}} + \frac{H_n^2(1)}{\alpha_{R\eta}}}.$$

With $A_{n\eta}$, $\beta_{n\eta}$, $\alpha_{L\eta}$, and $\alpha_{R\eta}$ known, $\tau_{M\eta}$ (which is the $\tau_M$ in the presence of absorption) is determined by modifying equation (57) and solving $$\Sigma_1 - \beta_n^4 A_n e^{-\beta_n^2 \tau_M}\left[\sin\beta_n - \frac{\alpha_L}{\beta_n}\cos\beta_n\right] = 0.$$

Then, the peak value time $t_{M\eta}$ determined according to the experiment is compared to the theoretical value with the ratio of the two ($t_{M\eta}/\tau_{M\eta}$) being equal to the time scale $T_T$ which is a function of the permeability k of the equilibration pressure.

Figure 12:
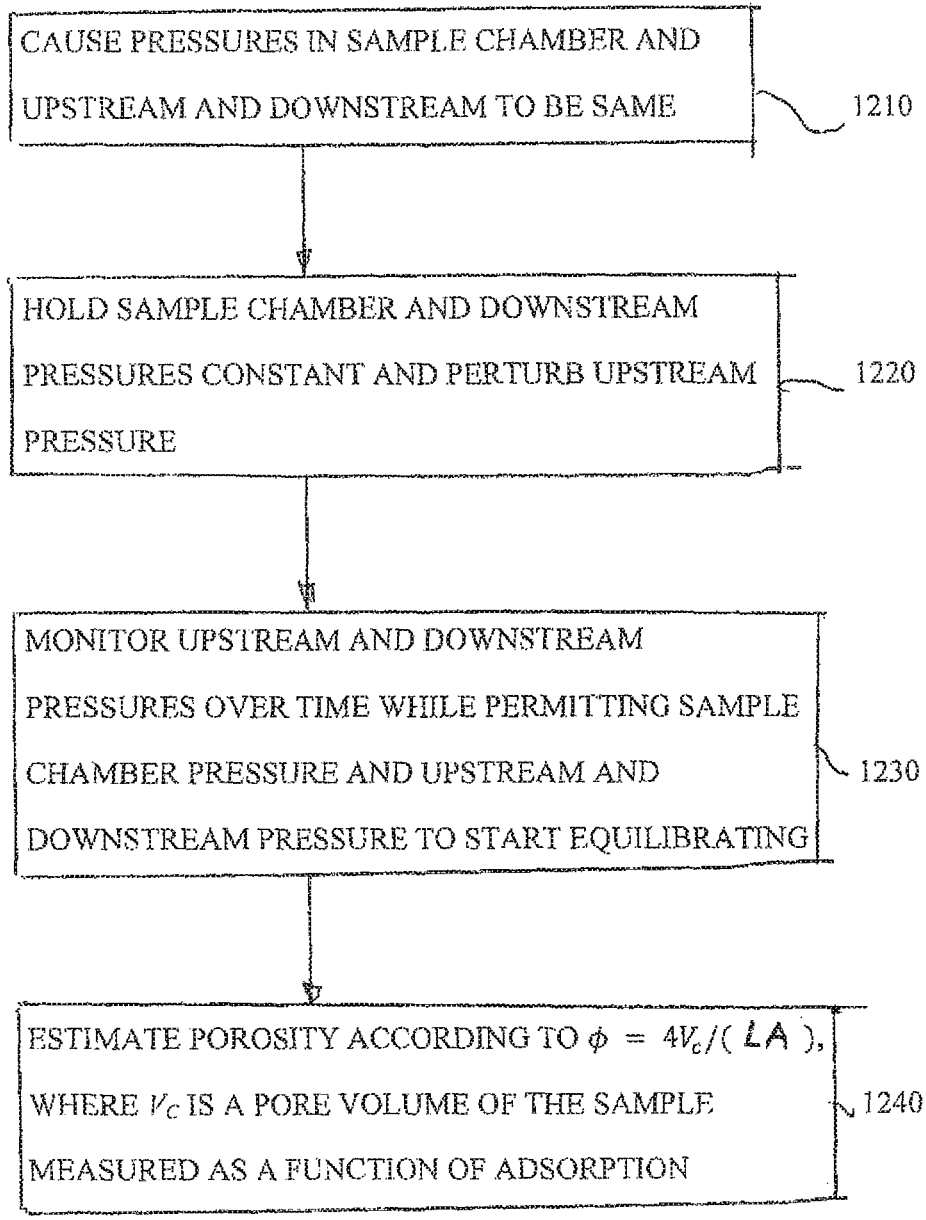
FIG. 12 is a flow diagram of a method of determining the porosity of an ultra-low permeable sample while accounting for adsorption.

According to another embodiment, the porosity of an ultra-low permeability sample contained in a sample chamber can be determined while accounting for adsorption. As seen in FIG. 12, at 1210 using a sample chamber as described above with reference to FIG. 1A or 1B, the pressures in the sample chamber and upstream and downstream of the sample chamber are caused to be the same. At 1220, the upstream pressure is changed by a perturbation percentage while holding the sample chamber and downstream pressures constant. At 1230, the upstream and downstream pressures are monitored as a function of time while permitting the sample chamber pressure and the upstream and downstream pressures to start equilibrating. At 1240, porosity $\phi$ is estimated according to the following relationship $\phi = 4V_c/(LA)$, where L is the length of the sample and A is the cross-sectional area of the sample. For a core sample with a circular cross-section, porosity $\phi$ is estimated according to the following relationship: $\phi = 4V_c/(\pi L D^2)$, where L and D are the length and diameter of the sample respectively. $V_c$ is a pore volume of the sample measured as a function of adsorption according to $V_c =$ $$V_L \frac{\left(\frac{P_f}{Z_f} - \frac{V_l P_{l0}}{V_L Z_{l0}} - \frac{V_h P_{R0}}{V_L Z_{R0}}\right)}{\left(\frac{P_{R0}}{Z_{R0}} - \frac{P_f}{Z_f} + \frac{RT}{M} c_\eta (P_{R0} - P_f)\right)} - V_R \frac{\left(\frac{P_{R0}}{Z_{R0}} - \frac{P_f}{Z_f}\right)}{\left(\frac{P_{R0}}{Z_{R0}} - \frac{P_f}{Z_f} + \frac{RT}{M} c_\eta (P_{R0} - P_f)\right)},$$

$V_L$ is a total volume upstream of the sample chamber, $V_R$ is a total volume downstream of the sample chamber, $P_f$ is an equilibrated pressure, $P_{R0}$ is the downstream pressure prior to a start of the equilibrating, $P_{L0}$ is the upstream pressure prior to a start of the equilibrating, $V_l$ is a calibrated volume of an upstream chamber, $V_h$ is a connection volume between the sample chamber and an upstream valve between the sample chamber and the upstream chamber, $c_\eta$ is a quasi-linear adsorption coefficient from the adsorption isotherm, and $Z_{l0}$, $Z_{R0}$, and $Z_f$ are compressibility factors. In one embodiment, the quasi-linear adsorption coefficient of the adsorption isotherm at pressure $P_f$ may be previously known, or may have previously been determined by bringing gas into contact with the ultra-low permeability sample and measuring the adsorption isotherm as a function of pressure.

There have been described and illustrated herein several embodiments of apparatus and methods of determining the permeability and/or porosity of an ultra-low permeability sample. While particular embodiments and aspects have been described, it is not intended that the disclosure be limited thereto, and it is intended that the claims be as broad in scope as the art will allow and that the specification be read likewise. Thus, while apparatus having a specific number of chambers of specific volumes were described, it will be appreciated that the volumes and numbers of those chambers could be different. Similarly, while experiments having particular radial stresses (squeeze pressures) on a sample were described, it will be appreciated that experiments may be run on samples to obtain permeabilities and/or porosities using different squeeze pressures. It will therefore be appreciated by those skilled in the art that yet other modifications could be made. Accordingly, all such modifications are intended to be included within the scope of this disclosure as defined in the following claims. In the claims, means-plus-function clauses, if any, are intended to cover the structures described herein as performing the recited function and not only structural equivalents, but also equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method of characterizing permeability of a sample located in a sample chamber, comprising:
   (a) causing a sample chamber pressure and an upstream and downstream pressure to be the same;
   (b) increasing the upstream pressure by a perturbation percentage while holding the sample chamber and downstream pressures constant;
   (c) monitoring the upstream and downstream pressures as a function of time while permitting the sample chamber pressure and the upstream and downstream pressures to start equilibrating;
   (d) finding a decay constant relating to the difference in the measured upstream and downstream pressures over time; and
   (e) utilizing the decay constant to determine a permeability estimate of the sample by accounting for adsorption of gas within the sample.

2. The method according to claim 1, wherein the sample has a permeability of less than 100 mD.

3. The method according to claim 1, wherein the sample is a core sample taken from a geological formation.

4. The method of claim 1, wherein adsorption of the sample is accounted for by using an adsorption isotherm of the sample.

5. The method of claim 4, further comprising:
   performing an experiment on the sample to determine the adsorption isotherm of the sample.

6. The method of claim 4, wherein the permeability estimate is generated according to the relationship:

$$k = \frac{\mu \phi L^2 G_f}{\beta_{1\eta}^2 P_f T_d} \left(1 + \frac{c_\eta P_f}{E_f G_f} \frac{RT}{M}\right),$$

where k is the permeability estimate, $\phi$ is the porosity of the sample, $\mu$ is the shear or dynamic viscosity of a gas used in permitting the sample chamber pressure and the upstream and downstream pressures to start equilibrating, L is the length of the sample, $\beta_{1\eta}$ is a first eigenvalue which is a function of adsorption, $G_f$ is related to a compressibility factor of the gas, $P_f$ is an estimated or measured final equilibration pressure, $E_f$ is a ratio of gas pressure to compressibility factor at pressure $P_f$, $c_\eta$ is a quasilinear adsorption coefficient obtained from the adsorption isotherm of the sample at pressure $P_f$, R is the gas constant, T is temperature, M is the molecular weight of the gas, and $T_d$ is the decay constant.

7. A method of characterizing permeability of a sample located in a sample chamber, comprising:
   (a) causing a sample chamber pressure and an upstream and downstream pressure to be the same;
   (b) causing a pressure perturbation so that the downstream pressure is lower than at least one of the upstream pressure and the sample chamber pressure;
   (c) monitoring the downstream pressure as a function of time while permitting the upstream and downstream pressures to start equilibrating;
   (d) finding a peak value time of a derivative of the downstream pressure signal; and
   (e) using the peak value time to determine a permeability estimate of the sample by accounting for adsorption of gas within the sample.

8. The method of claim 7, wherein the using the peak value time of a derivative comprises relating the peak value time and a porosity value for the sample to a permeability of the sample.

9. The method of claim 8, wherein the relating the peak value time and a porosity value comprises utilizing a crossplot having derivative-peak time as one axis, permeability as another axis, and a plurality of curves relating to different porosity values.

10. The method of claim 7, wherein the using a peak value time comprises estimating a theoretical value $\tau_{M_n}$ of a dimensionless peak value time, and comparing the peak value time $t_{M_n}$ to the theoretical value wherein a ratio of the peak value time and the theoretical value is a time scale that is a function of the permeability k of the equilibration pressure and the porosity $\phi$ of the sample.

11. The method of claim 10, wherein the ratio of the peak value time and the theoretical value time is $$t_{M\eta}/\tau_{M\eta} = \frac{\phi L^2 G_f}{\lambda_f P_f},$$

where L is the length of the sample, $G_f$ is related to a compressibility factor of a gas used in generating the upstream pressure, $P_f$ is an estimated equilibration pressure, and $\lambda_f = k/\mu$ where $\mu$ is the viscosity of the gas.

12. The method of claim 11, further comprising monitoring the upstream pressure as a function of time, wherein the $P_f$ is estimated or determined from the upstream and the downstream pressures as a function of time.

13. The method of claim 12, wherein the $P_f$ is estimated or determined from an average of the upstream and the downstream pressures.

14. A method of characterizing porosity of a sample located in a sample chamber, comprising:

(a) causing a sample chamber pressure and an upstream and downstream pressure to be the same;

(b) increasing the upstream pressure by a perturbation percentage while holding the sample chamber and downstream pressures constant;

(c) monitoring the upstream and downstream pressures as a function of time while permitting the sample chamber pressure and the upstream and downstream pressures to start equilibrating;

(d) estimating the porosity $\phi$ according to the relationship: $\phi = 4V_c/(LA)$, where $V_c$ is a pore volume of the sample determined according to the relationship:

$$V_c = V_L \frac{\left(\frac{P_f}{Z_f} - \frac{V_l P_{l0}}{V_L Z_{l0}} - \frac{V_h P_{R0}}{V_L Z_{R0}}\right)}{\left(\frac{P_{R0}}{Z_{R0}} - \frac{P_f}{Z_f} + \frac{RT}{M}c_\eta(P_{R0} - P_f)\right)} - V_R \frac{\left(\frac{P_{R0}}{Z_{R0}} - \frac{P_f}{Z_f}\right)}{\left(\frac{P_{R0}}{Z_{R0}} - \frac{P_f}{Z_f} + \frac{RT}{M}c_\eta(P_{R0} - P_f)\right)},$$

where L and A are the length and cross-sectional area of the sample respectively, $V_L$ is a total volume upstream of the sample chamber, $V_R$ is a total volume downstream of the sample chamber, $P_f$ is an equilibrated pressure, $P_{R0}$ is the downstream pressure prior to a start of the equilibrating, $P_{l0}$ is the upstream pressure prior to a start of the equilibrating, $V_l$ is a calibrated volume of an upstream chamber, $V_h$ is a connection volume between the sample chamber and an upstream valve between the sample chamber and the upstream chamber, $c_\eta$ is a quasi-linear adsorption coefficient obtained from an adsorption isotherm of the sample at pressure $P_f$, $Z_{l0}$, $Z_{R0}$, and $Z_f$ are compressibility factors, M is a molecular weight of a gas used in permitting the sample chamber pressure and the upstream and downstream pressures to start equilibrating generating, R is a gas constant, and T is temperature.

15. The method of claim 14, further comprising finding $P_f$ by fitting a decay curve to at least one of the monitored upstream and downstream pressures over time.

16. The method of claim 14, further comprising setting $P_f$ equal to an average of the upstream pressure and the downstream pressure.

* * * * *